US010039478B2

(12) United States Patent
Kasahara et al.

(10) Patent No.: US 10,039,478 B2
(45) Date of Patent: Aug. 7, 2018

(54) BIOLOGICAL INFORMATION PROCESSING METHOD, BIOLOGICAL INFORMATION PROCESSING APPARATUS, COMPUTER SYSTEM, AND WEARABLE APPARATUS

(71) Applicant: SEIKO EPSON CORPORATION, Tokyo (JP)

(72) Inventors: Hirokazu Kasahara, Okaya (JP); Tsukasa Eguchi, Matsumoto (JP); Hideto Ishiguro, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 744 days.

(21) Appl. No.: 14/608,838

(22) Filed: Jan. 29, 2015

(65) Prior Publication Data
US 2015/0216458 A1    Aug. 6, 2015

(30) Foreign Application Priority Data

Jan. 31, 2014 (JP) ................................. 2014-017021

(51) Int. Cl.
*A61B 5/1455* (2006.01)
*A61B 5/145* (2006.01)
*A61B 5/00* (2006.01)

(52) U.S. Cl.
CPC ........ *A61B 5/14532* (2013.01); *A61B 5/1455* (2013.01); *A61B 5/742* (2013.01); *A61B 5/743* (2013.01); *A61B 5/6801* (2013.01); *A61B 5/681* (2013.01); *A61B 5/7207* (2013.01); *A61B 5/7221* (2013.01)

(58) Field of Classification Search
CPC ... A61B 5/14532; A61B 5/743; A61B 5/1455; A61B 5/742; A61B 5/7207; A61B 5/7221; A61B 5/6801; A61B 5/681
See application file for complete search history.

(56) References Cited

U.S. PATENT DOCUMENTS

| | | | |
|---|---|---|---|
| 6,725,074 B1 | 4/2004 | Kastle | |
| 7,142,901 B2 * | 11/2006 | Kiani | A61B 5/14535 600/331 |
| 7,167,736 B2 * | 1/2007 | Winther | A61B 5/14558 600/318 |
| 7,280,860 B2 | 10/2007 | Ikeda et al. | |

(Continued)

FOREIGN PATENT DOCUMENTS

| | | |
|---|---|---|
| EP | 0 282 234 A1 | 9/1988 |
| EP | 0 872 210 A1 | 10/1998 |

(Continued)

OTHER PUBLICATIONS

Jun. 19, 2015 European Search Report issued in European Application No. 15153020.1.

*Primary Examiner* — Eric Winakur
(74) *Attorney, Agent, or Firm* — Oliff PLC

(57) ABSTRACT

In a biological information processing apparatus, a variation index value calculation section calculates a variation index value on the basis of a plurality of measured values obtained by measuring biological information of a subject. A display data generation section generates display data which is used to display a measurement result and undergoes identification display corresponding to the variation index value.

11 Claims, 15 Drawing Sheets

(56) References Cited

U.S. PATENT DOCUMENTS

| | | | |
|---|---|---|---|
| 8,335,550 B2* | 12/2012 | Segman | A61B 5/1455 |
| | | | 600/322 |
| 2010/0081942 A1 | 4/2010 | Huiku | |
| 2010/0094096 A1 | 4/2010 | Petruzzelli et al. | |
| 2013/0030306 A1 | 1/2013 | Yamanaka et al. | |
| 2014/0121540 A1* | 5/2014 | Raskin | A61B 5/6898 |
| | | | 600/476 |

FOREIGN PATENT DOCUMENTS

| | | |
|---|---|---|
| JP | 2003-505120 A | 2/2003 |
| JP | 2006-247375 A | 9/2006 |
| JP | 4236950 B2 | 3/2009 |
| JP | 2014-124453 A | 7/2014 |
| JP | 2014-124454 A | 7/2014 |
| JP | 2014-124455 A | 7/2014 |

* cited by examiner

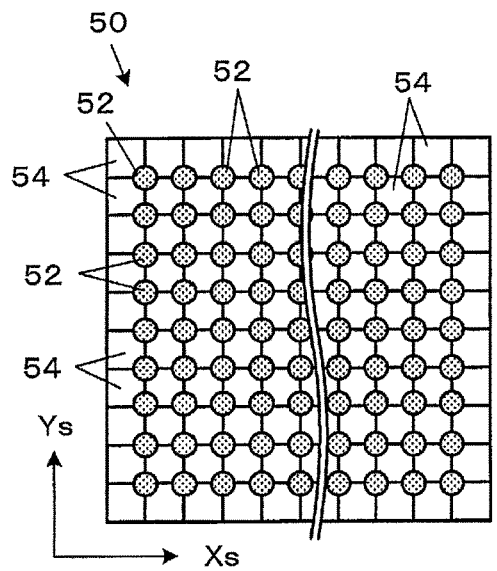
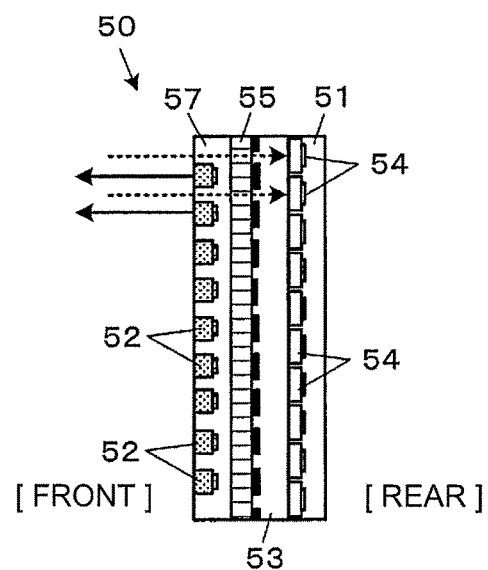
FIG. 2A  FIG. 2B
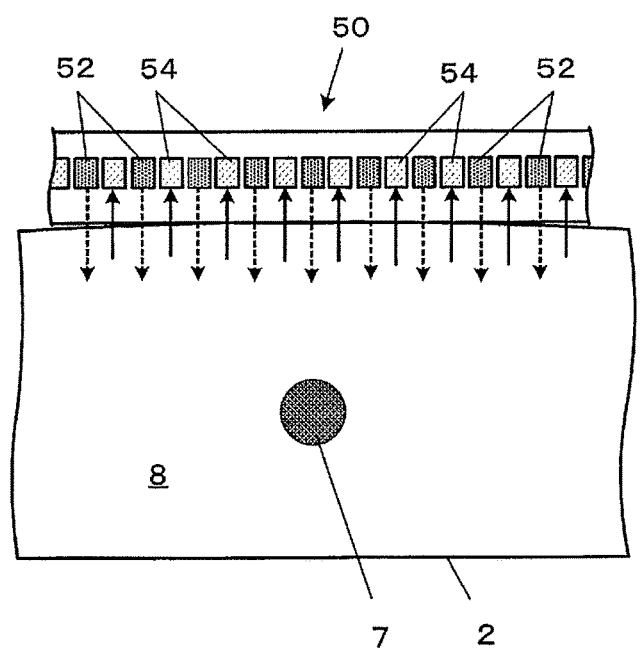
FIG. 3

| BLOOD VESSEL MEASUREMENT POINT NUMBER | IRRADIATION POSITION (MEASUREMENT LIGHT EMITTING ELEMENT) | MEASUREMENT LIGHT RECEPTION POSITION (MEASUREMENT LIGHT RECEIVING ELEMENT) |
|---|---|---|
| A_001 | xxxxx | xxxxx |
| A_002 | xxxxx | xxxxx |

| MEASUREMENT TIME | MEASUREMENT RESULT (BLOOD GLUCOSE LEVEL) | VARIATION RANGE UPPER LIMIT | VARIATION RANGE LOWER LIMIT |
|---|---|---|---|
| 2013/11/13 14:15 | 80 | 100 | 60 |
| 2013/11/13 14:16 | 80 | 100 | 60 |
| ⋮ | ⋮ | ⋮ | ⋮ |

BIOLOGICAL INFORMATION PROCESSING METHOD, BIOLOGICAL INFORMATION PROCESSING APPARATUS, COMPUTER SYSTEM, AND WEARABLE APPARATUS

CROSS REFERENCE

The entire disclose of Japanese Patent Application No. 2014-017021, filed Jan. 31, 2014, is expressly incorporated by reference herein.

BACKGROUND

1. Technical Field

The present invention relates to a biological information processing method and the like for processing biological information of a subject.

2. Related Art

In the related art, there is a measurement apparatus which measures biological information of a subject. As such a measurement apparatus, there is an apparatus which effectively uses a measurement result which is obtained by an external apparatus with a specification different from a dedicated specification, and can thus selectively display a highly accurate measurement result.

JP-A-2006-247375 is an example of the related art.

However, when biological information is measured, there is a case where measurement accuracy is reduced due to a factor such as a body motion of a subject and a measured value suddenly varies, despite an actual value not varying. For this reason, there is a desire to identify such a case from a case where an actual value varies. Particularly, in a case of measuring biological information which is essential for healthcare or life, for example, in a case of measuring a blood glucose level of a diabetic, since a sudden reduction in the blood glucose level is directly lead to a crisis of the life, to differentiate the cases from each other is important.

SUMMARY

An advantage of some aspects of the invention is to easily determine reliability of a measurement result.

A first aspect of the invention is directed to a biological information processing method including calculating a variation index value on the basis of a plurality of measured values obtained by measuring biological information of a subject; and generating display data which is used to display a measurement result and undergoes identification display corresponding to the variation index value.

As another aspect of the invention, the first aspect of the invention may be configured as a biological information processing apparatus including a calculation section that calculates a variation index value on the basis of a plurality of measured values obtained by measuring biological information of a subject; and a generation section that generates display data which is used to display a measurement result and undergoes identification display corresponding to the variation index value.

As still another aspect of the invention, the first aspect of the invention may be configured as a computer system which is connected to a wearable apparatus so as to perform communication therewith, the system including a calculation section that calculates a variation index value on the basis of a plurality of measured values obtained by measuring biological information of a user of the wearable apparatus; a generation section that generates display data which is used to display a measurement result and undergoes identification display corresponding to the variation index value; and a transmission control section that performs control for transmitting the display data to the wearable apparatus.

As still another aspect of the invention, the first aspect of the invention may be configured as a wearable apparatus including a calculation section that calculates a variation index value on the basis of a plurality of measured values obtained by measuring biological information of a user; and a display control section that performs identification display corresponding to the variation index value on a measurement result and controls display of the measurement result.

According to the first aspect and the another aspects, it is possible to calculate a variation index value of a plurality of pieces of biological information and to generate display data which undergoes identification display corresponding to the variation index value and is used to display a measurement result. By using the display data, it is possible to easily determine reliability of the measurement result.

A second aspect of the invention is directed to the biological information processing method according to the first aspect, wherein the measured value is obtained by applying irradiation waves toward a living body and measuring a predetermined living tissue state or a component in extracellular fluid, a plurality of measured values are obtained through a single measurement, and the calculating of the variation index value includes calculating the variation index value related to the single measurement.

According to the second aspect, it is possible to calculate a variation index value of a plurality of measured values which are obtained by measuring a predetermined living tissue state or a component in extracellular fluid and are obtained by performing a single measurement.

A third aspect of the invention is directed to the biological information processing method according to the second aspect, wherein the biological information processing method further includes storing a measurement result and the variation index value related to each measurement in correlation with a measurement time, and the generating of the display data includes generating data for displaying a graph which indicates a time-series change in a range corresponding to the variation index value and the measurement result related to each measurement.

According to the third aspect, it is possible to display a time-series change in a measurement result related to each measurement in a graph along with a range corresponding to a variation index value at a corresponding measurement time.

A fourth aspect of the invention is directed to the biological information processing method according to any one of the first to third aspects, wherein the biological information processing method further includes acquiring the plurality of measured values by measuring the biological information.

As another aspect of the invention, the forth aspect may be configured, as a ninth aspect of the invention, as the wearable apparatus which further includes a measurement section that obtains the measured value by applying irradiation waves toward a living body of a user and measuring a predetermined living tissue state or a component in extracellular fluid.

According to the fourth aspect and the another aspect, it is possible to acquire a plurality of measured values by measuring biological information such as a predetermined living tissue state or a component in extracellular fluid.

A fifth aspect of the invention is directed to the biological information processing method according to the second or third aspect, wherein the biological information processing method further includes acquiring the plurality of measured values by performing a measurement using either one of a first measurement method and a second measurement method in which at least measurement object sites are different from each other.

According to the fifth aspect, it is possible to acquire a plurality of measured values by measuring biological information by selectively using measurement methods in which at least measurement object sites are different from each other.

A sixth aspect of the invention is directed to the biological information processing method according to the fifth aspect, wherein the measurement includes performing a measurement using one of the first measurement method and the second measurement method according to priority which is set in advance, and switching to the other measurement method on the basis of the variation index value.

According to the sixth aspect, it is possible to select a measurement method to be applied according to preset priority and to switch a measurement method to be applied on the basis of a variation index value.

BRIEF DESCRIPTION OF THE DRAWINGS

The invention will be described with reference to the accompanying drawings, wherein like numbers reference like elements.

FIGS. 2A and 2B are diagrams illustrating a configuration example of a sensor module.

FIG. 3 is a conceptual diagram illustrating a method of acquiring a blood vessel position.

FIG. 10 is a diagram illustrating a data configuration example of an irradiation/light reception position list.

DESCRIPTION OF EXEMPLARY EMBODIMENTS

Figure 1:
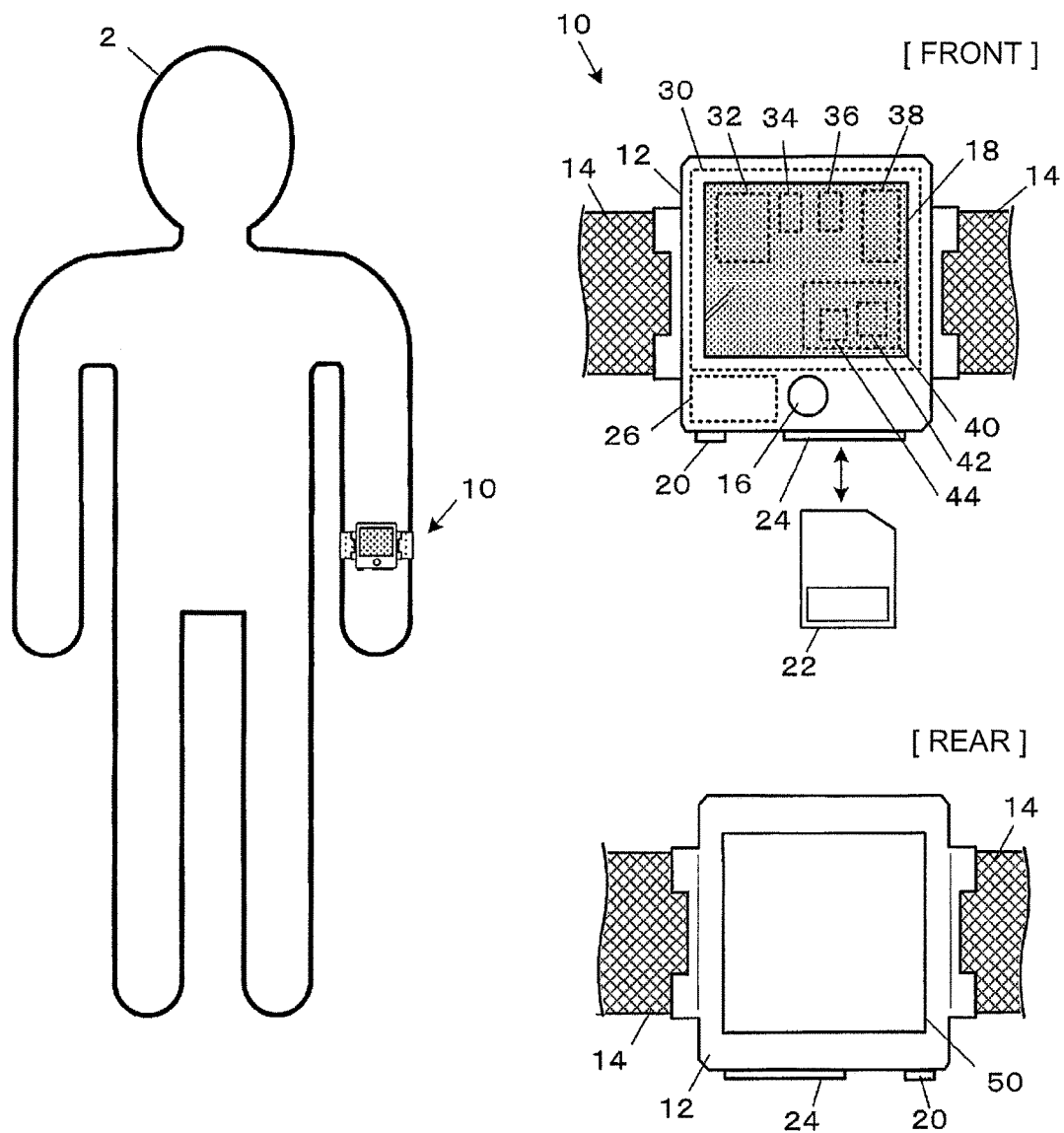
FIG. 1 is an exterior view illustrating an entire configuration example of a biological information processing apparatus.

Hereinafter, with reference to the drawings, a biological information processing method and the like according to embodiments of the invention will be described. In addition, the invention is not limited by the embodiments described below, and an applicable form of the invention is not limited to the following embodiments. Throughout the drawings, the same reference numerals are given to the same constituent elements.

First Embodiment

A first embodiment is an embodiment in which a so-called "blood glucose level" is measured as biological information of a subject, and a "blood vessel type" measurement is employed as a first measurement method. In a "blood vessel type" measurement, a blood vessel is set as a measurement object site, and a blood glucose level is obtained by measuring a glucose concentration in blood which is extracellular fluid.

Entire Configuration

FIG. 1 is an exterior view illustrating an entire configuration example of a non-invasive biological information processing apparatus 10 in the first embodiment. The biological information processing apparatus 10 functions as a measurement apparatus which measures a component of extracellular fluid such as blood or tissue fluid of a subject 2, and a data logger which stores measured data, and can be said to be a kind of computer. As illustrated in FIG. 1, the biological information processing apparatus 10 is constituted by, for example, a wrist watch type wearable apparatus, and is mounted on a body part such as the arm, the leg, the neck, or the like of the subject 2 with a band 14 provided in a main body case 12, so as to be used.

The biological information processing apparatus 10 is provided with an operation switch 16 and a touch panel 18 which is also used as an image display unit on a front surface (a surface directed outwards when the subject 2 wears the biological information processing apparatus 10) of the main body case 12 as an operation input unit. The subject 2 who is a user can input various operations such as a measurement start operation using the switch and panel.

A communication device 20 in which a wired cable for communication with external devices is attachable and detachable, and a reader/writer 24 which performs reading and writing data from and to a memory card 22 are provided on a side surface of the main body case 12. In addition, the sensor module 50 as a measurement unit which is a main sensor to apply measurement light toward a living body of the subject 2 as irradiation waves and receive reflected wave light, is provided on a rear surface (a surface which comes into contact with the skin of the subject 2 when the subject 2 wears the biological information processing apparatus 10) side of the main body case 12. A charging type internal battery 26 and a control board 30 are built into the main body case 12.

In a configuration in which communication with an external device is performed in a wireless manner, the communication device 20 is implemented by a wireless communication module and an antenna.

The memory card 22 is a data rewritable nonvolatile memory which is attachable and detachable. As the memory card 22, not only a flash memory, but also a rewritable nonvolatile memory such as a ferroelectric random access memory (FeRAM) or a magnetoresistive random access memory (MRAM) may be used.

A type of charging the internal battery 26 may be set as appropriate. For example, there may be a configuration in which an electric contact is separately provided on the rear surface side of the main body case 12, the main body case 12 is set in a cradle connected to a domestic power supply, and the battery 26 is conducted and charged via the electric contact and the cradle, or the battery 26 may be charged in a non-contact manner.

The control board 30 collectively controls the biological information processing apparatus 10. Specifically, the control board 30 is equipped with a central processing unit (CPU) 32, a main memory 34, a measurement data memory 36, a touch panel controller integrated circuit (IC) 38, and a sensor module controller 40. In addition, the control board 30 may be equipped with an electronic component such as a power supply management IC or an image processing IC as appropriate.

The main memory 34 is a storage medium which can store a program, initial setting data, or a calculation value of the CPU 32. The main memory 34 is implemented by using a RAM, a ROM, a flash memory, or the like as appropriate. The program or the initial setting data may be stored in the memory card 22.

The measurement data memory 36 is a data rewritable nonvolatile memory and is a storage medium which stores measurement data of a blood glucose level. As the measurement data memory 36, not only a flash memory, but also a rewritable nonvolatile memory such as a ferroelectric random access memory (FeRAM) or a magnetoresistive random access memory (MRAM) may be used. The measurement data may be stored in the memory card 22.

The touch panel controller IC 38 is an IC which realizes a driver function for displaying an image on the touch panel 18 and realizes a touch input function. The touch panel controller IC 38 and the touch panel 18 can be implemented by using a well-known technique as appropriate.

The sensor module controller 40 includes an IC or a circuit having a function of causing the sensor module 50 to apply measurement light and an IC or a circuit having a function of causing the sensor module 50 to receive light (transmitted light) which is a result of the measurement light being transmitted through a biological tissue of the subject or light (reflected light) which is a result of the measurement light being reflected in the biological tissue.

More specifically, the sensor module controller 40 includes a light emission controller 42 constituted by an IC or a circuit which individually controls light emission of a plurality of light emitting elements (elements emitting measurement light through conduction) provided in the sensor module 50, and a light reception controller 44 constituted by an IC or a circuit which controls light reception of a plurality of light receiving elements (elements outputting an electric signal corresponding to an amount of received light) provided in the sensor module 50.

The sensor module controller 40 may be constituted by a plurality of ICs. For example, different ICs may be used as an IC or a circuit corresponding to the light emission controller 42 and an IC or a circuit corresponding to the light reception controller 44. Alternatively, some of the functions may be realized by the CPU 32.

FIGS. 2A and 2B are diagrams illustrating a configuration of the sensor module 50. FIG. 2A is a plan view and FIG. 2B is a cross-sectional view. For better understanding, a light emitting element 52 or a light receiving element 54 is intentionally enlarged and illustrated. A size and an aspect ratio are not limited thereto, and may be set as appropriate.

The sensor module 50 is a device formed by laminating a layer in which a plurality of light emitting elements 52 are arranged in a planar shape and a layer in which a plurality of light receiving elements 54 are arranged in a planar shape. In other words, the sensor module 50 is an image sensor with a light source, and is a sensor array which realizes both functions of irradiation and light reception of measurement light. The sensor module 50 may be integrally formed with the sensor module controller 40.

The light emitting elements 52 are an irradiation unit which applies measurement light, and may be implemented by, for example, light emitting diodes (LEDs) or organic light emitting diodes (OLEDs). In a case of measuring a blood glucose level, the light emitting elements 52 employ elements which can emit light including near infrared rays having subcutaneous transparency close to a visible region.

The light receiving elements 54 are imaging elements which receive transmitted light or reflected light of the measurement light and output an electric signal corresponding to a light reception amount. For example, the light receiving elements 54 may be implemented by semiconductor elements such as charge coupled device (CCD) image sensors or complementary metal oxide semiconductor (CMOS) image sensors. A single light receiving element 54 is assumed to include a plurality of elements which receive RGB wavelength components.

The sensor module 50 is a device in which 1) a light receiving layer 51, 2) a light blocking layer 53, 3) a spectroscopic layer 55, and 4) a light emitting layer 57 are laminated in this order from a base side (the front side of the main body case 12). A plurality of light receiving elements 54 are arranged in a planar shape or in a lattice shape in the light receiving layer 51. The light blocking layer 53 selectively blocks light which is not directed to each light receiving element 54, and the spectroscopic layer 55 selectively transmits near infrared rays therethrough. A plurality of light emitting elements 52 are arranged in a planar shape or a lattice shape at positions which are located between adjacent light receiving elements 54 and do not impede optical paths along which light transmitted through or reflected in a biological tissue reaches the light receiving elements 54 in the light emitting layer 57.

The light receiving elements 54 of the light receiving layer 51 are disposed in a matrix in which pixels can be identified with an Xs-Ys orthogonal coordinate system, such as a well-known CCD image sensor. In other words, the sensor module 50 functions in the same manner as the well-known image sensor. A shape, a size, and an arrangement pattern of the light receiving elements 54 may be set as appropriate.

Each of the light emitting elements 52 of the light emitting layer 57 is disposed at butted parts of corners of the adjacent light receiving elements 54 when the sensor module 50 is viewed from the front side (the rear side of the main body case 12). More specifically, a single light emitting element 52 is disposed at the butted parts of the corners of the four light receiving elements 54, and the whole light emitting elements 52 are disposed in a matrix which can be identified with the Xs-Ys orthogonal coordinate system in the same manner as the light receiving elements 54. The sensor module 50 includes a driving mechanism which causes the light emitting elements 52 to selectively emit light, and driving of the light emitting elements 52 can be controlled in the same manner as in an active matrix of a liquid crystal panel display.

A well-known semiconductor micro-processing technique used for manufacturing of a CCD image sensor or an OLED display may be applied as appropriate to manufacturing of the sensor module 50 having such a laminate structure.

A size or an arrangement interval of the light emitting elements 52 and a size or an arrangement interval of the light receiving elements 54 may be set as appropriate. For example, an arrangement interval of 1 to 500 [μm] is preferably used, and, for example, 50 to 200 [μm] may be used from the viewpoint of manufacturing cost and measurement accuracy. In order to narrow an irradiation range of measurement light applied from the light emitting elements 52 or to polarize the measurement light, or in order to accurately correct light transmitted through or reflected in a biological tissue at the light receiving elements 54, a light collecting layer having an optical element may be further provided in the sensor module 50. In addition, a protective layer for preventing a surface damage may be provided as appropriate. The light emitting elements 52 and the light receiving elements 54 are not only laminated but may also be arranged in parallel to each other.

Overview

The biological information processing apparatus 10 is fixed with the band 14 so that the rear surface to which the sensor module 50 is exposed is brought into close contact with the skin of the subject 2. Since the sensor module 50 is brought into close contact with the skin, it is possible to minimize factors which reduce measurement accuracy, such as reflection of measurement light at the skin surface or scattering thereof near the skin surface.

As a measurement procedure of a blood glucose level in the "blood vessel type", first, a blood vessel under the skin of the body covered with the sensor module 50 is selected as a measurement object site. In addition, the selected blood vessel is irradiated with measurement light as a target and light is received. Then, a blood vessel transmitted light component which has been transmitted through the blood vessel is extracted from a light reception result (intensity of received light), and a glucose concentration is calculated as a blood glucose level on the basis of a relative spectrum (absorption spectrum) which reflects an amount of the blood vessel transmitted light component.

In order to select a blood vessel as a measurement object site and a position thereof, it is necessary to identify where a blood vessel is present under the skin covered with the sensor module 50. FIG. 3 is a conceptual diagram illustrating a method of acquiring a blood vessel position, and corresponds to a cross-sectional view of a portion of the subject 2 covered with the sensor module 50. The sensor module 50 is simply illustrated.

When a blood vessel position is acquired, first, in the same manner as in vein pattern detection in a well-known vein authentication technique, the light emitting layer 52 of the sensor module 50 are made to simultaneously emit light so as to irradiate the entire location where the sensor module 50 is mounted with measurement light. In addition, light which has been transmitted through or reflected in a biological tissue (subcutaneous tissue) under the skin is collected (an image is captured) by using all the light receiving elements 54, so as to acquire a biological image.

Here, the biological image acquired by the sensor module 50 becomes a set of luminance data of pixels which respectively correspond to the light receiving elements 54 of the sensor module 50, and can be obtained as a two-dimensional image of the Xs-Ys orthogonal coordinate system in the same manner as pixel coordinates of the sensor module 50. The blood vessel more easily absorbs near infrared rays than a biological tissue portion (hereinafter, referred to as a "non-blood vessel part") other than the blood vessel, due to an influence of blood which flows therethrough. For this reason, the blood vessel has lower luminance and is darker than the non-blood vessel part. Therefore, if a location whose luminance is lower is extracted from the biological image, it is possible to identify whether the blood vessel is reflected or the non-blood vessel part is reflected in each pixel, that is, whether or not the blood vessel is present under each of the light receiving elements 54.

Figure 4:
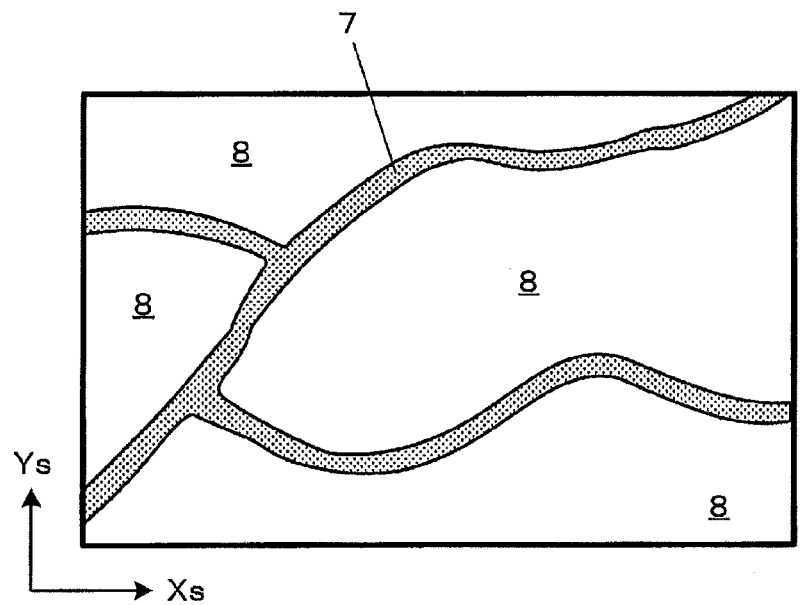
FIG. 4 is a diagram schematically illustrating a biological image.

FIG. 4 is a diagram schematically illustrating a biological image. In an example of FIG. 4, a strip-shaped region hatched with a diagonal or dotted pattern indicates the blood vessel 7, and a white region indicates the non-blood vessel part 8. In addition, a method of acquiring a blood vessel position is not limited to the exemplified method. For example, there may be a method in which a relative position of an inner structure of a living body is acquired in advance by using a well-known biological tomographic image measurement technology such as ultrasonic echo, magnetic resonance imaging (MRI), or computed tomography (CT), and a blood vessel position is determined on the basis thereof.

If the position of the blood vessel 7 is acquired, a process (a blood vessel type irradiation/light reception position selection process) of selecting an irradiation position of measurement light (measurement light emitting element) and a measurement light reception position (measurement light receiving element) suitable for receiving transmitted light (blood vessel transmitted light) of the blood vessel 7 is performed.

Figure 5:
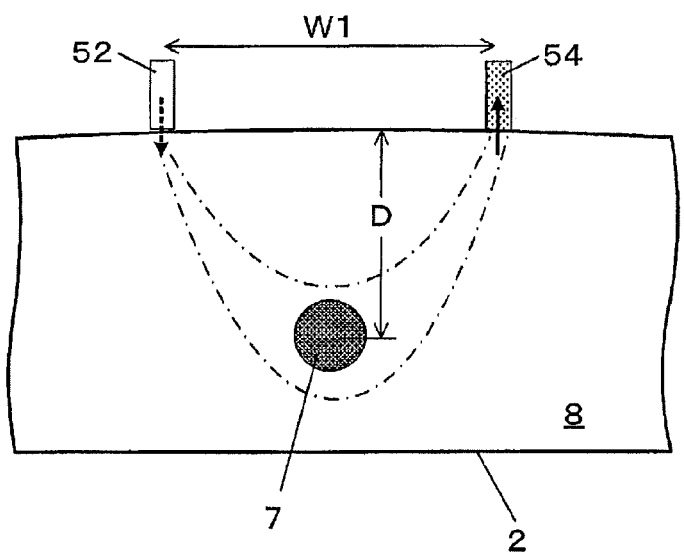
FIG. 5 is a diagram illustrating propagation of light in a biological tissue.

FIG. 5 is a diagram for explaining propagation of light in a biological tissue, and is a cross-sectional view in a depth direction. Light applied from a certain light emitting element 52 is diffused and reflected inside the biological tissue, and some of the applied light reaches a certain light receiving element 54. A propagation path of the light forms a so-called banana shape (a region interposed between two arcs), a width in the depth direction is largest in the vicinity of approximately a center thereof. The depth (reachable depth) of the propagation depth is increased as a gap between the light emitting element 52 and the light receiving element 54 becomes larger, and the depth is reduced as the gap therebetween becomes smaller.

Here, in order to increase measurement accuracy, it is desirable that a larger amount of blood vessel transmitted light is received by the light receiving element 54. From this factor, the optimum gap (optimum distance) W1 between the light emitting element 52 and the light receiving element 54 may be defined according to an expected depth D of the blood vessel 7 (a distance from the skin surface to the center of the blood vessel) on the condition that the blood vessel 7 is located nearly at a center between the light emitting element 52 and the light receiving element 54. The optimum distance W1 is a distance which approximately doubles a depth D of the blood vessel 7. For example, if the depth D is about 3 mm, the optimum distance W1 is about 5 mm to 6 mm.

Therefore, in the blood vessel type irradiation/light reception position selection process, blood vessel type relative position condition employs that "the blood vessel 7 is located at a center between an irradiation position and a measurement light reception position, and a distance between the irradiation position and the measurement light reception position is the same as the predetermined optimum distance W1", light emitting elements 52 and light receiving elements 54 satisfying the blood vessel type relative position condition are searched for, and are selected as an irradiation position and a measurement light reception position.

Figure 6:
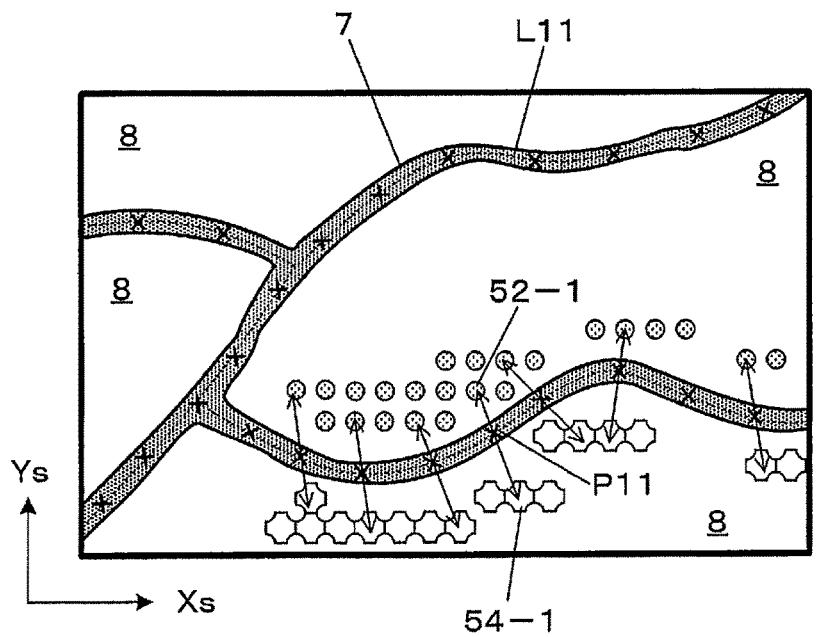
FIG. 6 is a diagram for explaining a blood vessel type irradiation/light reception position selection process.

FIG. 6 is a diagram for explaining a blood vessel type irradiation/light reception position selection process. In the blood vessel type irradiation/light reception position selection process, first, measurement points (blood vessel measurement points) are temporarily set along the blood vessel 7. For example, as indicated by an "X" mark in FIG. 6, blood vessel measurement points are temporarily set at predetermined intervals on a central line L11 of the blood vessel 7. A light emitting element 52 and a light receiving element 54 satisfying the blood vessel type relative position condition for each temporarily set blood vessel measurement point are searched for, and if there are elements satisfying the conditions, the light emitting element 52 is set as a measurement light emitting element 52-1, and the light receiving element 54 is set as a measurement light receiving element 54-1. Through this blood vessel type irradiation/light reception position selection process, a plurality of blood vessel measurement points P11 are set in which the light emitting elements 52 and the light receiving elements 54 satisfying the blood vessel type relative position condition are present, and an irradiation position and a measurement light reception position are selected for each of the blood vessel measurement points P11.

Then, if the blood vessel measurement point P11 is set, and the irradiation position and the measurement light reception position are selected for each blood vessel measurement point P11, a blood glucose level is measured. In other words, measurement light is applied from all irradiation positions (the measurement light emitting elements 52-1), and then a blood vessel transmitted light component is extracted from a light reception result at each measurement light reception position (the measurement light receiving element 54-1). In this case, for example, a wavelength of light emitted by the light emitting element 52 is changed so that a wavelength λ of measurement light is changed within a near infrared region, and thus an optical spectrum (absorption spectrum) of blood vessel transmitted light which has been transmitted through the blood vessel 7 is generated for each wavelength λ. Then, a blood glucose level is calculated (estimated) on the basis of the absorption spectrum by using a "calibration curve" indicating a relationship between a predefined glucose concentration in blood and an absorbance. In addition, as a technique for generating an absorption spectrum and calculating a concentration of a predetermined component (for example, a glucose concentration) on the basis of the absorption spectrum, a well-known technique may be employed as appropriate. Through the process here, a plurality of measured values can be obtained with one measurement.

In addition, measurement procedures are not particularly limited, and there may be a configuration in which all combinations of the light emitting elements 52 and the light receiving elements 54 are sequentially selected, and then measurements are performed.

Figure 7:
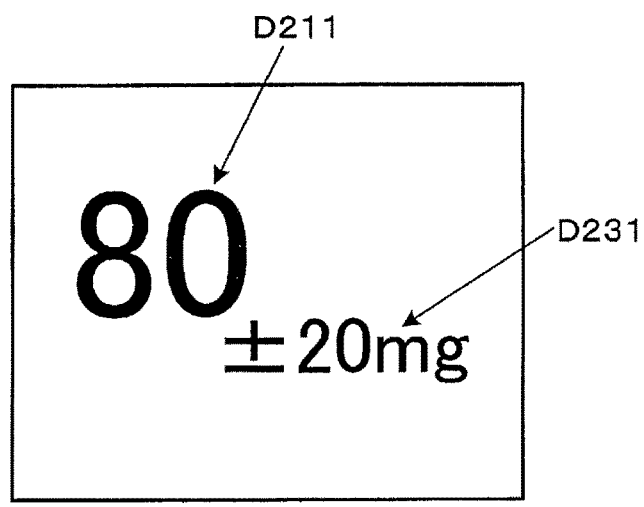
FIG. 7 is a diagram illustrating a display screen example of display data in a first embodiment.

Next, a variation index value is calculated on the basis of blood glucose levels (a plurality of measured values related to a single measurement) calculated for each of the blood vessel measurement points P11, display data undergoing identification display corresponding to the variation index value is generated, and a measurement result is displayed. In the first embodiment, a standard deviation (±σ) of the blood glucose levels for each of the blood vessel measurement points P11 is calculated as the variation index value. In addition, a mean value (μ) is used as a measurement result, and display data for displaying the mean value (μ) along with the standard deviation (±σ) is generated and is displayed. FIG. 7 is a diagram illustrating a display screen example of the display data in the first embodiment. In an example of FIG. 7, a variation index value D231 based on the standard deviation (±σ) is displayed near a measurement result D211 which is the mean value (μ).

Figure 8A:
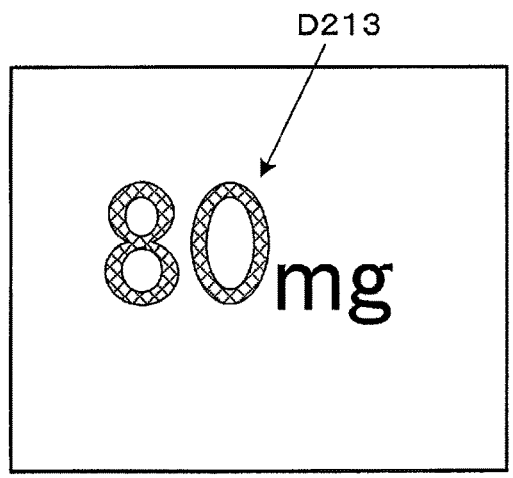
FIGS. 8A to 8C are diagrams illustrating other display screen examples of display data.
Figure 8B:
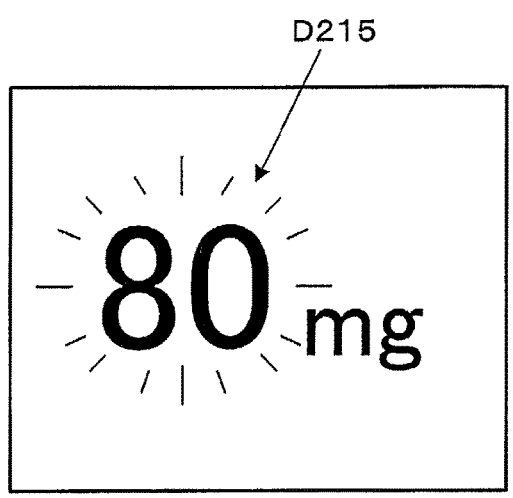
Figure 8C:
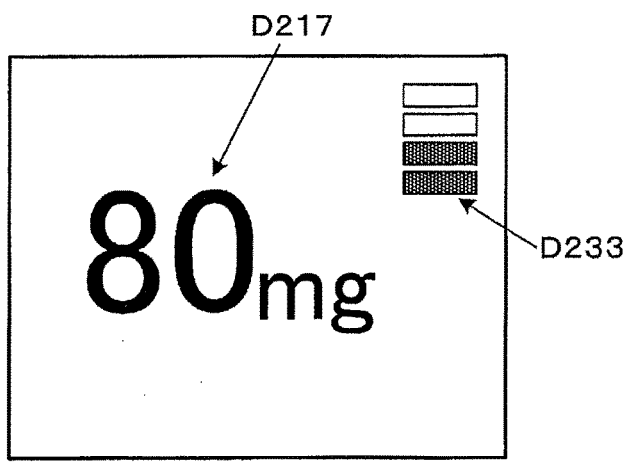

In addition, an identification display aspect of a measurement result is not limited to the identification display aspect illustrated in FIG. 7. FIGS. 8A to 8C are diagrams illustrating display screen examples of display data according to other identification display aspects. For example, different display colors may be set in advance in correlation with stepwise threshold values, and a display color of a measurement result D213 may be changed according to a variation index value (FIG. 8A). For example, with the highest accuracy which can be realized as a first threshold value (±5 mg/dl), with accuracy which does not cause practical inconveniences as a second threshold value (±20 mg/dl), accuracy which requires re-measurement in circumstances accompanied by a risk such as low blood glucose as a third threshold value (±50 mg/dl), and with a state in which the third threshold value is exceeded and a measured value cannot be reliable as a fourth threshold value, different display colors are set in correlation with the first to fourth threshold values of the respective stages. In this case, for example, display data for displaying a mean value (μ) in a display color corresponding to a standard deviation (±σ) is generated and displayed.

Alternatively, a measurement result D215 may be displayed in a blinking manner according to a variation index value (FIG. 8B). For example, different blinking patterns may be set in correlation with the first to fourth threshold values, and display data for displaying a mean value (μ) in a blinking pattern corresponding to a value of the standard deviation (±σ) is generated and displayed. In addition, a meter D233 which visually indicates the magnitude of a variation index value may be displayed around a measured value D217 (FIG. 8C). As described above, identification display may be performed on the measurement result D213 or D215 according to a variation index value (FIGS. 8A and 8B), and display data for identification display such as the above-described meter D233 may be generated around a position where a measured value is displayed according to a variation index value, separately from display data for a measurement result (FIGS. 7 and 8C).

Functional Configuration

Figure 9:
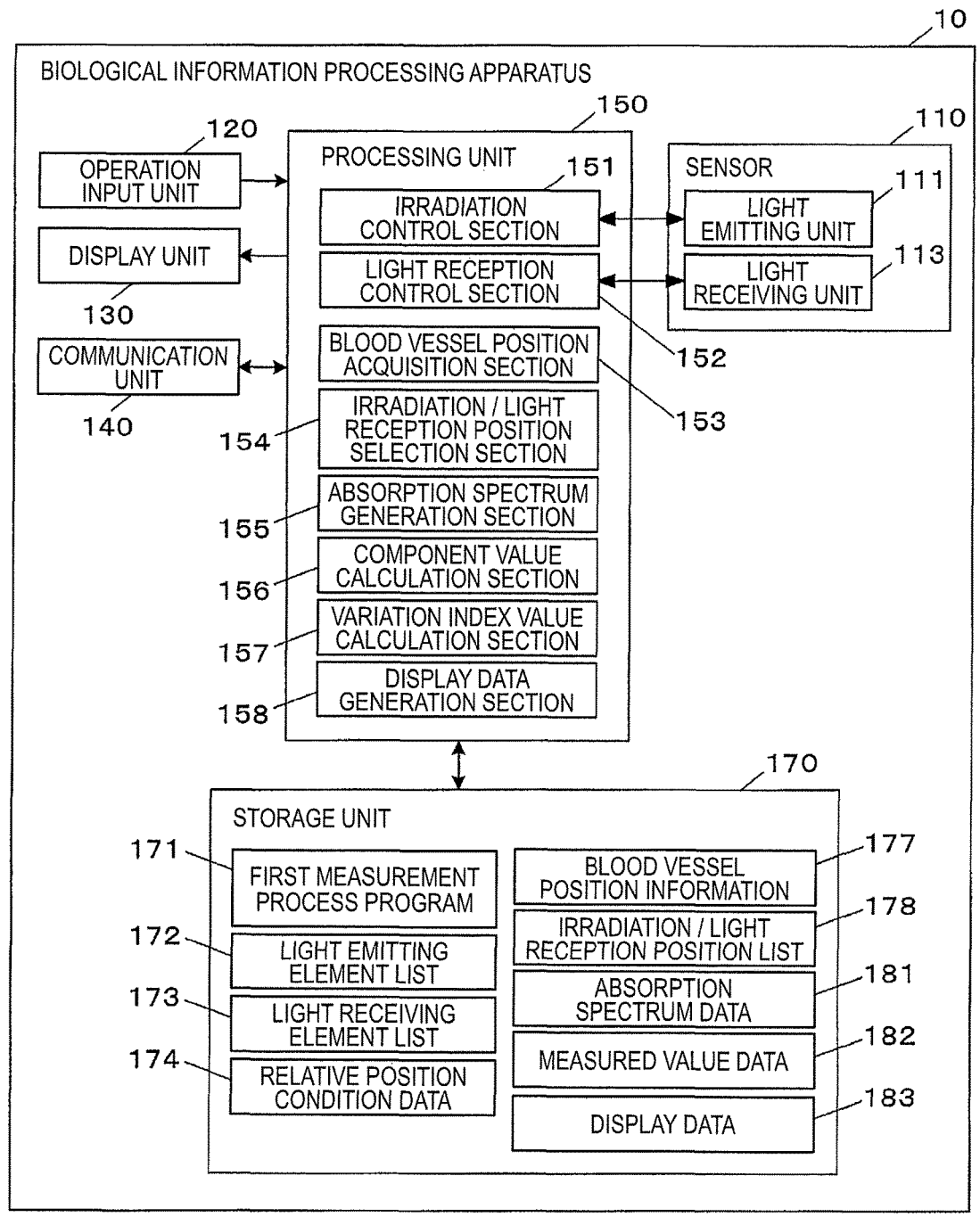
FIG. 9 is a block diagram illustrating a functional configuration example of a biological information processing apparatus in the first embodiment.

FIG. 9 is a block diagram illustrating a main functional configuration example of the biological information processing apparatus 10 in the first embodiment. As illustrated in FIG. 9, the biological information processing apparatus 10 includes a sensor 110, an operation input unit 120, a display unit 130, a communication unit 140, a processing unit 150, and a storage unit 170.

The sensor 110 corresponds to the sensor module 50 of FIGS. 2A and 2B, and includes a light emitting unit 111 constituted by a plurality of light emitting elements 52 and a light receiving unit 113 constituted by a plurality of light receiving elements 54. An arrangement position (Xs-Ys coordinate value) of each of the light emitting elements 52 forming the light emitting unit 111 is stored in advance as a light emitting element list 172 correlated with a light emitting element number assigned to a corresponding light emitting element 52 in the storage unit 170. In addition, an arrangement position (Xs-Ys coordinate value) of each of the light receiving elements 54 forming the light receiving unit 113 is stored in advance as a light receiving element list 173 correlated with a light receiving element number assigned to a corresponding light receiving element 54 in the storage unit 170.

The operation input unit 120 is implemented by using an input device such as various switches including a button switch or a dial switch, or a touch panel, and outputs an operation input signal corresponding to an operation performed by a user to the processing unit 150. The operation switch 16 and the touch panel 18 of FIG. 1 correspond to the operation input unit 120.

The display unit 130 is implemented by using a display device such as a liquid crystal display (LCD) or an electroluminescence (EL) display, and displays various screens on the basis of display signals input from the processing unit 150. The touch panel 18 of FIG. 1 corresponds to the display unit 130.

The communication unit 140 is a communication device which transmits and receives information used in the apparatus to and from an external information processing apparatus under the control of the processing unit 150. The communication device 20 of FIG. 1 corresponds to the communication unit 140. As a communication method of the communication unit 140, various types may be employed, such as a form in which wired connection is made via a cable conforming to a predetermined communication standard, a form in which connection is made via an intermediate device which is also used as a charger called a cradle, and a form in which wireless connection is made by using wireless communication.

The processing unit 150 is implemented by a microprocessor such as a central processing unit (CPU) or a digital signal processor (DSP), and a control device and a calculation device such as an application specific integrated circuit (ASIC), and collectively controls the respective units of the biological information processing apparatus 10. The control board 30 of FIG. 1 corresponds to the processing unit 150. The processing unit 150 includes an irradiation control section 151, a light reception control section 152, a blood vessel position acquisition section 153, an irradiation/light reception position selection section 154, an absorption spectrum generation section 155, a component value calculation section 156, a variation index value calculation section 157 as a calculation section, and a display data generation section 158 as a generation section. In addition, the respective sections forming the processing unit 150 may be constituted by hardware such as dedicated module circuits.

The irradiation control section 151 individually controls light emission of the light emitting elements 52 forming the light emitting unit 111. For example, the control may be realized by using a so-called active matrix driving control technique. The light reception control section 152 performs control for outputting an electric signal corresponding to an intensity of light received by the light receiving elements 54 of the light receiving unit 113.

The blood vessel position acquisition section 153 acquires a biological image (refer to FIG. 4) of a tissue under the skin covered with the sensor module 50, and acquires a blood vessel position by performing an image process on the biological image. The acquisition of the blood vessel position is performed by using a technique of capturing a biological image in a well-known vein authentication technique or the like, or by using a technique for identifying a vein pattern from a biological image in the well-known vein authentication technique or the like, as appropriate.

The irradiation/light reception position selection section 154, which is a functional section which performs a blood vessel type irradiation/light reception position selection process, searches for a light emitting element 52 and a light receiving element 54 satisfying a blood vessel type relative position condition for each blood vessel measurement point which is temporarily set along a blood vessel, so as to set a plurality of blood vessel measurement points on the blood vessel, and selects an irradiation position (the measurement light emitting element 52-1) and a measurement light reception position (the measurement light receiving element 54-1). Data regarding the blood vessel type relative position condition including the optimum distance W1 is stored as relative position condition data 174 in the storage unit 170 in advance.

The absorption spectrum generation section 155 applies measurement light from the measurement light emitting element 52-1 set as an irradiation position, under the control of the irradiation control section 151 and the light reception control section 152, and generates an absorption spectrum for each blood vessel measurement point on the basis of a light reception result obtained by the measurement light receiving element 54-1 set as a measurement light reception position.

The component value calculation section 156 calculates a glucose concentration in blood, which is an aimed component for each blood vessel measurement point on the basis of the absorption spectrum. For example, a blood glucose level is calculated from the absorption spectrum by using an analysis method such as a multiple regression analysis method, a main component regression analysis method, a PLS regression analysis method, or an independent component analysis method.

The variation index value calculation section 157 calculates a variation index value on the basis of a standard deviation ($\pm\sigma$) of blood glucose levels at each blood vessel measurement point. For example, a value obtained by multiplying a value of the standard deviation by a predetermined coefficient may be used as the variation index value, and the variation index value may be calculated by using a predetermined function having a value of the standard deviation as a variable. In addition, the standard deviation may be used as the variation index value.

The display data generation section 158 generates display data which has a mean value ($\mu$) of blood glucose levels at each blood vessel measurement point as a measurement result and undergoes identification display corresponding to a variation index value, and performs control for displaying the display data on the display unit 130.

The storage unit 170 is implemented by using various integrated circuit (IC) memories such as a read only memory (ROM), a flash ROM, or a random access memory (RAM) or a hard disk. The storage unit 170 stores a program for operating the biological information processing apparatus 10 and realizing various functions of the biological information processing apparatus 10, data used during execution of the program, or the like, in advance, or temporarily stores data each time a process is performed. In FIG. 1, the main memory 34 or the measurement data memory 36 mounted on the control board 30, and the memory card 22 correspond to the storage unit 170.

The storage unit 170 stores in advance a first measurement process program 171, the light emitting element list 172, the light receiving element list 173, and the relative position condition data 174. The first measurement process program 171 causes the processing unit 150 to function as the irradiation control section 151, the light reception control section 152, the blood vessel position acquisition section 153, the irradiation/light reception position selection section 154, the measurement method selection section 155, the absorption spectrum generation section 155, the component value calculation section 156, the variation index value calculation section 157, and the display data generation section 158, so as to perform a first measurement process (refer to FIG. 11).

In addition, the storage unit 170 stores blood vessel position information 177, an irradiation/light reception position list 178, absorption spectrum data 181, measured value data 182, and display data 183 when a measurement is performed.

The irradiation/light reception position list 178 stores an irradiation position and a measurement light reception position selected as a result of the blood vessel type irradiation/light reception position selection process. FIG. 10 is a diagram illustrating a data configuration example of the irradiation/light reception position list 178. As illustrated in FIG. 10, the irradiation/light reception position list 178 is a data table in which an irradiation position and a measurement light reception position are set in correlation with a blood vessel measurement point number. A light emitting element number of a corresponding light emitting element 52, that is, the measurement light emitting element 52-1 is registered in the irradiation position, and a light receiving element number of a corresponding light receiving element 54, that is, the measurement light receiving element 54-1 is registered in the measurement light reception position.

Flow of Process

Figure 11:
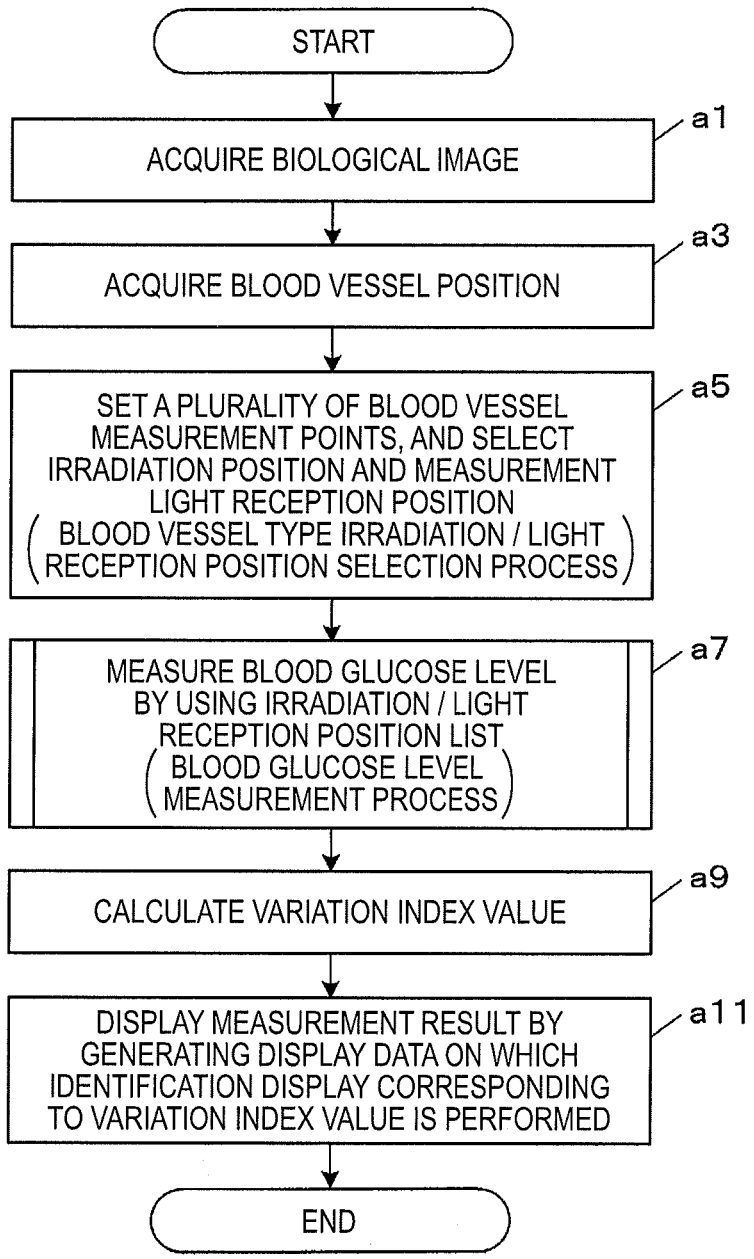
FIG. 11 is a flowchart illustrating process procedures of a first measurement process.

FIG. 11 is a flowchart illustrating process procedures of the first measurement process. The process described here may be performed by the processing unit 150 reading and executing the first measurement process program 171 from the storage unit 170. The first measurement process is started when the biological information processing apparatus 10 is mounted on the body of the subject 2, and a predetermined measurement start operation is input thereto.

As illustrated in FIG. 11, in the first measurement process, first, the irradiation control section 151 causes the light emitting elements 52 of the sensor module 50 to simultaneously emit light, and the light reception control section 152 causes all the light blocking layer 54 to receive light (an image is captured), so that a biological image is acquired (step a1). Next, the blood vessel position acquisition section 153 performs an image process on the biological image so as to acquire a blood vessel which is viewed from the skin surface (step a3). For example, the blood vessel position acquisition section 153 performs a binarization or a filtering process on each pixel of the acquired biological image (luminance image) through comparison with reference luminance, so as to acquire a blood vessel position. A pixel having luminance lower than the reference luminance indicates a blood vessel and a pixel having equal to or lower than the reference luminance indicates a non-blood vessel part. The acquired blood vessel position is stored as the blood vessel position information 177 in the storage unit 170.

Next, the irradiation/light reception position selection section 154 performs the blood vessel type irradiation/light reception position selection process so as to set a plurality of blood vessel measurement points on the blood vessel, and selects an irradiation position and a measurement light reception position (step a5). At this time, the irradiation/light reception position selection section 154 assigns a blood vessel measurement point number to each blood vessel measurement point, and generates the irradiation/light reception position list 178 by correlating a light emitting element number of the measurement light emitting element 52-1 and a light receiving element number of the measurement light receiving element 54-1 therewith. Then, a blood glucose level measurement process is performed by using the irradiation/light reception position list 178 (step a7).

Figure 12:
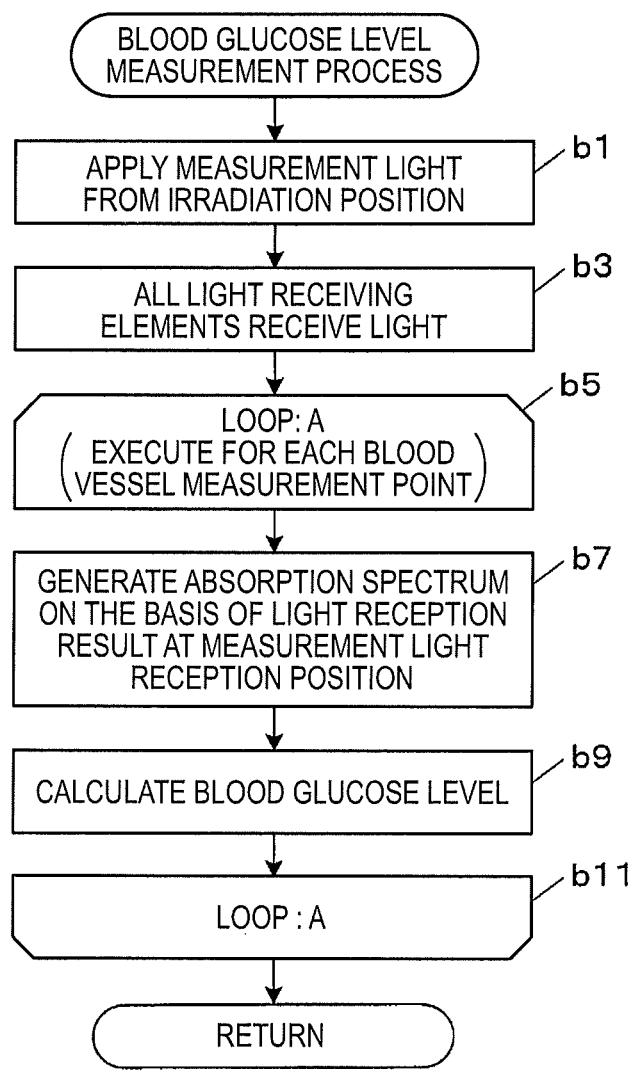
FIG. 12 is a flowchart illustrating specific process procedures of a blood glucose level measurement process.

FIG. 12 is a flowchart illustrating specific process procedures of the blood glucose level measurement process. As illustrated in FIG. 12, in the blood glucose level measurement process, the irradiation control section 151 causes the irradiation positions to simultaneously emit light according to the irradiation/light reception position list 178 (step b1), and the light reception control section 152 causes all the light receiving elements 54 to receive light (step b3). Then, a process of a loop A is performed for each blood vessel measurement point (step b5 to step b11). In other words, first, the absorption spectrum generation section 155 refers to the irradiation/light reception position list 178, and generates an absorption spectrum on the basis of light reception results at corresponding measurement light reception positions at respective measurement points correlated with blood vessel measurement point numbers of process objects (step b7). The spectrum data regarding the generated absorption spectrum is stored as the absorption spectrum data 181 in the storage unit 170. The component value calculation section 156 calculates a blood glucose level on the basis of the absorption spectrum generated in step b7 (step b9). The calculated blood glucose level is accumulated and stored as measured value data 182 in correlation with a blood vessel measurement point number of a process object in the storage unit 170.

If the blood glucose level measurement process is completed, the flow returns to step a7 of FIG. 11 and then proceeds to step a9. The variation index value calculation section 157 calculates a variation index value by using the measured value data 182 (step a9), and the display data generation section 158 generates the display data 183 so as to display a measurement result (step a11). For example, the variation index value calculation section 157 calculates a variation index value on the basis of a standard deviation ($\pm\sigma$) which is calculated on the basis of the blood glucose levels at each blood vessel measurement point, and the display data generation section 158 performs control for displaying a mean value ($\mu$) of the blood glucose levels at each blood vessel measurement point along with the variation index value on the display unit 130.

As described above, according to the first embodiment, blood glucose levels can also be measured at a plurality of blood vessel measurement points which are set as a result of acquiring blood vessel positions, and a standard deviation thereof can be calculated as a variation index value. In addition, it is possible to generate and display the display data which has a mean value of blood glucose levels measured at each blood vessel measurement point as a measurement result and undergoes identification display corresponding to the variation index value.

If a variation between blood glucose levels (measured values) at each blood vessel measurement point, which are simultaneously measured, is small, reliability of a measurement result is high. In contrast, if a variation index value is great, a value which causes low measurement accuracy (large measurement error) is included, and thus as the variation index value becomes greater, reliability of a measurement result is reduced. As measurement accuracy reducing factors, there may be a case where a blood vessel position under the skin mismatches an acquired blood vessel position due to a mounting location of the sensor module 50 being deviated by a body motion, a case where a blood vessel position is not accurately specified, a case where noise is much, and the like.

Therefore, for example, when a measurement result is an abnormal value, an identification display aspect, in which display of a variation index value displayed near a measurement result, a display color of the measurement result, a blinking pattern, gauge display of the variation index value, and the like indicate a great variation index value, can be determined as being caused by measurement errors. In contrast, in a case of an identification display aspect indicating a small variation index value, it can be visually identified at a glance that a state of the subject 2 is abnormal. As mentioned above, a measurement result having undergone identification display corresponding to a variation index value is generated as display data and is displayed, and thus it is possible to easily determine reliability of the measurement result. As a result, it is possible to accurately make a diagnosis.

Second Embodiment

A second embodiment may be fundamentally realized in the same manner as the first embodiment, but is different in that a blood glucose level is repeatedly measured at a predetermined measurement timing such as every one minute during a predetermined period (for example, a day or the like). The second embodiment is an embodiment which assumes a use aspect of the biological information processing apparatus 10 which is mounted on the subject 2 for a relatively long period of time so as to be used.

Figure 13:
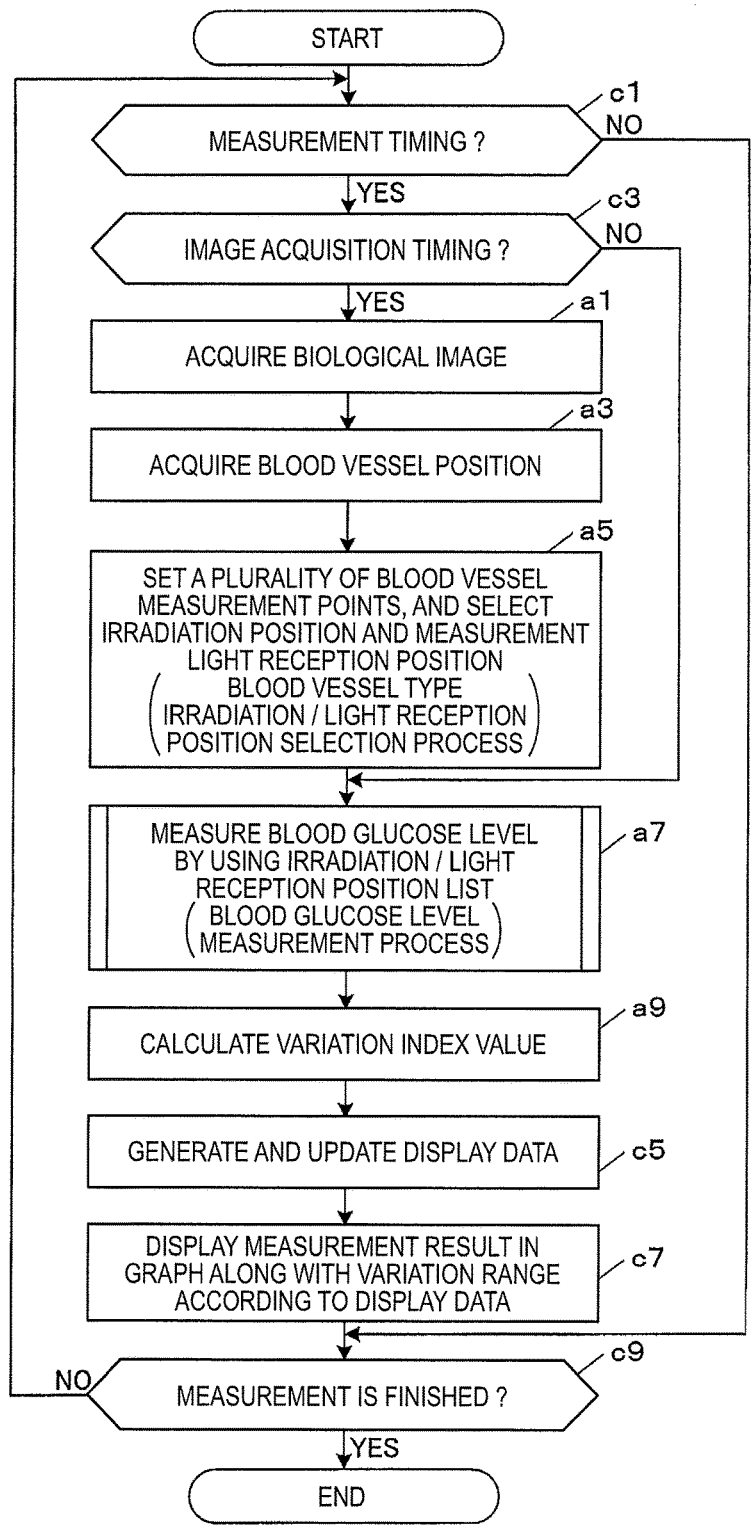
FIG. 13 is a flowchart illustrating process procedures of a second measurement process.
Figures 14, 15:
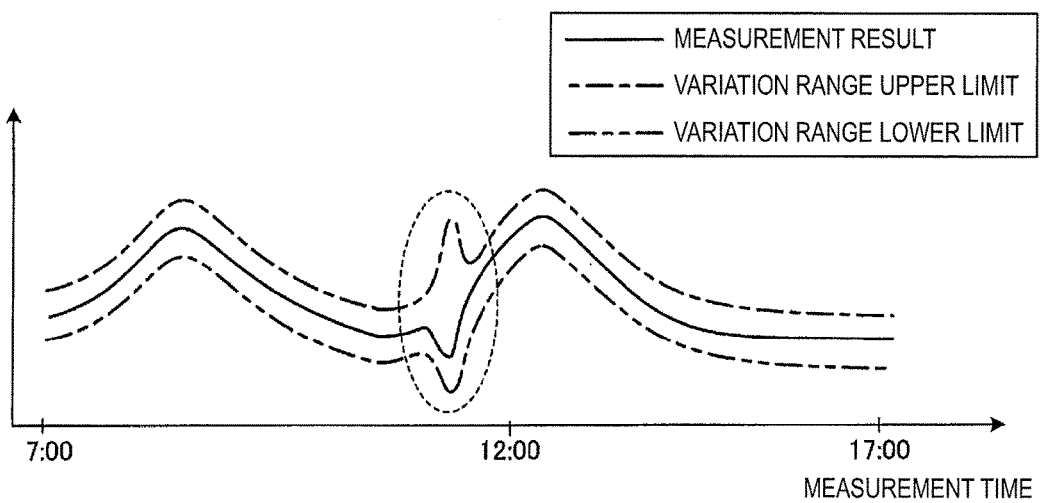
FIG. 14 is a configuration example of display data in a second embodiment.
FIG. 15 is a diagram illustrating a display screen example of display data in the second embodiment.

FIG. 13 is a flowchart illustrating a flow of a process (second measurement process) of the processing unit 150 in the second embodiment. The second embodiment may be realized by storing a second measurement process program for realizing the second measurement process in the storage unit 170 instead of the first measurement process program 171 in the biological information processing apparatus 10 of the first embodiment illustrated in FIG. 9. In the second embodiment, instead of the display data 183 of FIG. 9, display data 183a of FIG. 14 is stored in the storage unit 170. In FIG. 13, the same process steps as in the first embodiment are given the same reference numerals.

As illustrated in FIG. 13, in the second measurement process, first, a standby state occurs until a measurement timing arrives (step c1: NO). For example, in a case where a measurement is performed every one minute, the time at which one minute has elapsed from the previous measurement timing is determined as a measurement timing (step c1: YES), and then it is determined whether or not an image acquisition timing arrives. If it is determined that the image acquisition timing arrives (step c3: YES), the flow proceeds to step a1. If the image acquisition timing does not arrives (step c3: NO), the flow proceeds to step a7. Here, the image acquisition timing may be, for example, ten minutes, and may be one hour, but if biological images are frequently captured at short intervals and blood vessel positions are acquired, measurement accuracy can be maintained. In contrast, as the interval is set to become longer, power consumption can be reduced. However, in a case where a blood vessel position under the skin does not match an acquired blood vessel position or a blood vessel cannot be accurately specified due to a mounting location of the sensor module 50 being deviated, a measurement cannot be accurately performed until the next blood vessel position is acquired. The image acquisition timing is appropriately set in consideration of this situation.

In the second embodiment, a variation index value is calculated in step a9, and then the display data generation section 158 generates and updates the display data 183a (step c5). FIG. 14 is a diagram illustrating a configuration example of the display data 183a in the second embodiment. As illustrated in FIG. 14, the display data 183a of the second embodiment is a data table in which a measurement result, a variation range upper limit, and a variation range lower limit are set in correlation with a measurement time.

In step c5 of FIG. 13, the display data generation section 158 calculates a mean value of blood glucose levels at each blood vessel measurement point as a result of the measurement. In addition, the display data generation section 158 rearranges the blood glucose levels (measured values) at each blood vessel measurement point in a descending order, and excludes measured values corresponding to top 10% and measured values corresponding to bottom 10%. Further, among remaining measured values, the greatest measured value is set as the variation range upper limit, and the smallest measured value is set as the variation range lower limit, which are then obtained as variation index values. In this case, the display data generation section 158 generates a record which has the present time as the measurement date and time and correlates a measurement result, the variation range upper limit, and the variation range lower limit with each other, so as to add the record to the display data 183a for update.

In subsequent step c7, the display data generation section 158 performs control so that a graph indicating a time-series change in a variation range and a measurement result according to the display data 183a generated and updated in step c5 is displayed on the display unit 130. Then, the flow returns step c1 and the above-described processes are repeatedly performed until the measurements are finished (step c9: NO).

FIG. 15 is a diagram illustrating a display screen example of display data in the second embodiment. As illustrated in FIG. 15, in the second embodiment, a range (variation range) defined by the variation range upper limit indicated by a dot chain line and the variation range lower limit indicated by a two-dot chain line is a range corresponding to a variation index value, and is displayed in a graph along with a measurement result indicated by a solid line.

Here, in the example of FIG. 15, a measurement result at a measurement time (about 11:30) surrounded by a dashed line sharply decreases. On the other hand, the lower limit of the variation range decreases along with the measured value, but the upper limit thereof increases, and thus the variation range sharply widens. Therefore, it can be determined that the variation in this measurement result is caused not by an abnormal state of the subject 2 but by many blood glucose levels reducing measurement accuracy being included in blood glucose levels at each blood vessel measurement point, obtained as measured values at a corresponding measurement time (measurement errors). As mentioned above, according to the second embodiment, it is possible to easily determine reliability of a measurement result.

The display data described in the first embodiment and the display data described in the second embodiment may be displayed in a switching manner. During a measurement, the display data of the first embodiment may be displayed, and, after the measurement is finished, the display data of the second embodiment may be displayed. For example, in diagnosis and analysis after the measurement, in order to diagnose a medical condition or to evaluate medicinal effects on the basis of a blood glucose level variation during a predetermined period such as one day or one month, the display data of the second embodiment may be referred to.

Third Embodiment

In the third embodiment, the "blood vessel type" measurement described in the first embodiment and a "non-blood vessel type" measurement as a second measurement method are performed in a switching manner. In the "non-blood vessel type", a non-blood vessel part is used as a measurement object site, and a blood glucose level is obtained by measuring a glucose concentration in tissue fluid which is extracellular fluid. In addition, the same portions as in the first embodiment or the second embodiment are given the same reference numerals.

In the "blood vessel type" in which a measurement object site is a blood vessel, a blood glucose level can be measured with high accuracy. On the other hand, since a region of the blood vessel is narrow, a blood vessel position acquired by capturing a biological image in advance tends not to match a blood vessel position in an actual measurement. As a factor thereof, there may be a case where a mounting location of a sensor module 50 described later is deviated due to a body motion of a subject 2, or a case where a blood vessel moves due to a body motion. In such a case, a blood vessel is deviated from a target, and thus measurement accuracy is considerably reduced. Therefore, there is disadvantageous in that a measurement result may not be stably provided in the "blood vessel type" measurement.

In contrast, in the "non-blood vessel type" in which a measurement target site is a non-blood vessel part, a rapid change in a blood glucose level is hardly detected compared with the "blood vessel type", and accordingly measurement accuracy is reduced, but a region of the non-blood vessel part (specifically, a dermal layer) is wide, and thus the non-blood vessel part is scarcely deviated from a measurement target unlike in the "blood vessel type" even if a mounting location of the sensor module 50 is deviated. For this reason, there is advantageous in that a measurement can be performed with stable accuracy in the "non-blood vessel type" measurement.

In the "non-blood vessel type", a non-blood vessel part under the skin of the body covered with the sensor module 50 is selected as a measurement object site. In addition, the selected non-blood vessel part is irradiated with measurement light as a target and light is received. Then, a non-blood vessel part transmitted light component which has been transmitted through the non-blood vessel part is extracted from a light reception result, and a blood glucose level is calculated on the basis of an absorption spectrum which reflects an amount of the non-blood vessel part transmitted light component.

In the "non-blood vessel type", prior to a measurement, a process (a non-blood vessel type irradiation/light reception position selection process) of selecting an irradiation position of measurement light (measurement light emitting element) and a measurement light reception position (measurement light receiving element) suitable for receiving transmitted light (non-blood vessel transmitted light) which has been transmitted through a non-blood vessel part is performed. In the non-blood vessel type irradiation/light reception position selection process, a non-blood vessel type relative position condition employs that "a blood vessel is not present between an irradiation position and a measurement light reception position and a distance between the irradiation position and the measurement light reception position is the same as the optimum distance W2", a light emitting element 52 and a light receiving element 54 satisfying the non-blood vessel type relative position condition are searched for, and are selected as an irradiation position and a measurement light reception position.

Figure 16:
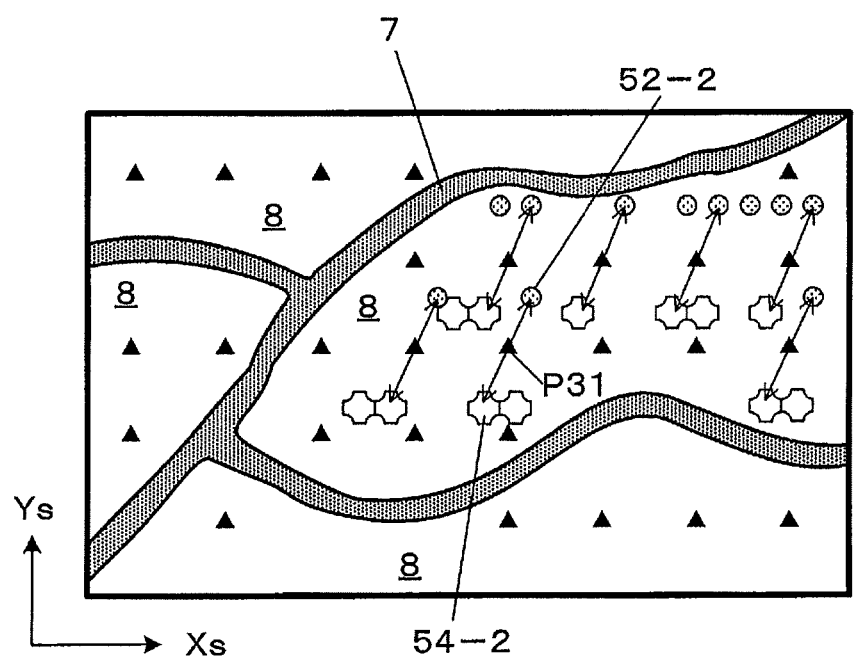
FIG. 16 is a diagram illustrating a non-blood vessel type irradiation/light reception position selection process.

FIG. 16 is a diagram for explaining the non-blood vessel type irradiation/light reception position selection process. In the non-blood vessel type irradiation/light reception position selection process, as indicated by a black "triangle" in FIG. 16, non-blood vessel part measurement points are temporarily set with a predetermined gap on the non-blood vessel part 8. A light emitting element 52 and a light receiving element 54 satisfying the non-blood vessel type relative position condition for each temporarily set non-blood vessel part measurement point are searched for, and if there are elements satisfying the conditions, the light emitting element 52 is set as a measurement light emitting element 52-2, and the light receiving element 54 is set as a measurement light receiving element 54-2. The optimum distance W2 may be set in advance in accordance with a reaching depth (a depth from the skin surface of the dermal layer) suitable to measure tissue fluid. Through this non-blood vessel type irradiation/light reception position selection process, a plurality of non-blood vessel part measurement points P31 are set in which the light emitting elements 52 and the light receiving elements 54 satisfying the non-blood vessel type relative position condition are present, and an irradiation position and a measurement light reception position are selected for each of the non-blood vessel part measurement points P31.

Next, a blood glucose level is measured. In other words, measurement light is applied from all irradiation positions (the measurement light emitting elements 52-2), and then a blood vessel transmitted light component is extracted from a light reception result at each measurement light reception position (the measurement light receiving element 54-2), so that an absorption spectrum is generated. Then, a blood glucose level is calculated (estimated) on the basis of the absorption spectrum by using a "calibration curve" indicating a relationship between a predefined a glucose concentration in blood and an absorbance.

In the "non-blood vessel type", the measurement may be performed so as to avoid the blood vessel 7, and may be performed on the dermal layer which is located further toward the skin surface than the blood vessel 7. Therefore, the invention is not limited to a case where the non-blood vessel part measurement points P31 are set on the non-blood vessel part 8 as illustrated in FIG. 16. For example, a measurement point may be set over the blood vessel 7, and an irradiation position and a measurement light reception position may be selected at positions where a reaching depth is smaller than an expected depth of the blood vessel 7.

Functional Configuration

Figure 17:
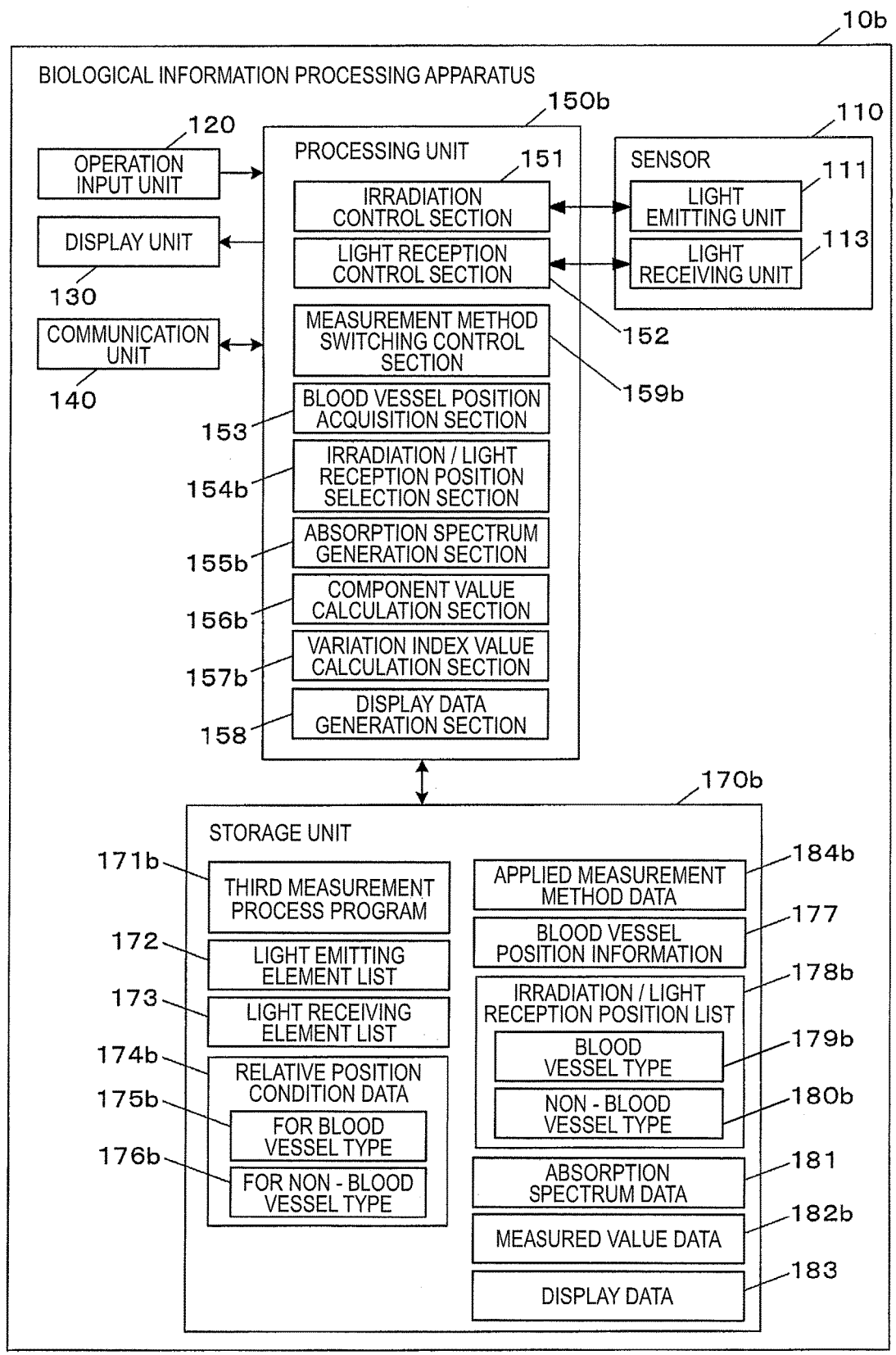
FIG. 17 is a block diagram illustrating a functional configuration example of a biological information processing apparatus in a third embodiment.

FIG. 17 is a block diagram illustrating a main functional configuration example of a biological information processing apparatus 10b in the third embodiment. As illustrated in FIG. 17, the biological information processing apparatus 10b includes a sensor 110, an operation input unit 120, a display unit 130, a communication unit 140, a processing unit 150b, and a storage unit 170b.

In the third embodiment, the processing unit 150b includes an irradiation control section 151, a light reception control section 152, a measurement method switching control section 159b, a blood vessel position acquisition section 153, an irradiation/light reception position selection section 154b, an absorption spectrum generation section 155b, a component value calculation section 156b, a variation index value calculation section 157b, and a display data generation section 158.

The measurement method switching control section 159b performs control so that a measurement method which is set to the highest priority in advance is selected and applied when a measurement is started, and is switched to a measurement method having lower priority so as to be applied according to a variation index value which is calculated by the variation index value calculation section 157 at any time during the measurement. In the third embodiment, the measurement method includes a "blood vessel type" and a "non-blood vessel type", and the priority of the "blood vessel type" is set to be higher.

The irradiation/light reception position selection section 154b performs the blood vessel type irradiation/light reception position selection process described in the first embodiment in a "blood vessel type" measurement. On the other hand, the irradiation/light reception position selection section 154b performs a non-blood vessel type irradiation/light reception position selection process in a "non-blood vessel type" measurement. In other words, the irradiation/light reception position selection section 154b searches for a light emitting element 52 and a light receiving element 54 satisfying the non-blood vessel part relative position condition for each non-blood vessel part measurement point which is temporarily set in a non-blood vessel part so as to set a plurality of non-blood vessel part measurement points on the non-blood vessel part, and selects an irradiation position (measurement light emitting element 52-2) and a measurement light reception position (measurement light emitting element 54-2). Data regarding the blood vessel type relative position condition is stored as data for the blood vessel type 175b, and data regarding the non-blood vessel type relative position condition including the optimum distance W2 is stored as data regarding the non-blood vessel type 176b, and the two data items are stored in advance as relative position condition data 174b in the storage unit 170b.

When an absorption spectrum is generated, the absorption spectrum generation section 155b refers to the data for the blood vessel type 179b in the "blood vessel type", and refers to the data for the non-blood vessel type 180b in the "non-blood vessel type", so as to use the irradiation/light reception position list in a switching manner. Consequently, the absorption spectrum generation section 155b applies measurement light from the measurement light emitting element 52-1 or the measurement light emitting element 52-2 set as an irradiation position, under the control of the irradiation control section 151 and the light reception control section 152. The absorption spectrum generation section 155b generates an absorption spectrum for each blood vessel measurement point or generates an absorption spectrum for each non-blood vessel part measurement point, on the basis of a light reception result obtained by the measurement light receiving element 54-1 or the measurement light emitting element 54-2 set as a measurement light reception position.

The component value calculation section 156b calculates a glucose concentration in blood or tissue fluid, which is an aimed component for each blood vessel measurement point or for each non-blood vessel part measurement point on the basis of the absorption spectrum.

By using measured value data 182b, the variation index value calculation section 157b calculates a variation index value on the basis of blood glucose levels at each blood vessel measurement point in the "blood vessel type", and calculates a variation index value on the basis of blood glucose levels at each non-blood vessel part measurement point in the "non-blood vessel type".

The storage unit 170b stores in advance a third measurement process program 171b, the light emitting element list 172, the light receiving element list 173, and the relative position condition data 174b. The third measurement process program 171b causes the processing unit 150b to function as the irradiation control section 151, the light reception control section 152, the measurement method switching control section 159b, the blood vessel position acquisition section 153, the irradiation/light reception position selection section 154b, the measurement method selection section 155b, the absorption spectrum generation section 155b, the component value calculation section 156b, the variation index value calculation section 157b, and the display data generation section 158, so as to perform a third measurement process (refer to FIG. 18).

In addition, the storage unit 170b stores applied measurement method data 184b, blood vessel position information 177, an irradiation/light reception position list 178b, absorption spectrum data 181, measured value data 182b, and display data 183 when a measurement is performed.

The applied measurement method data 184b stores a measurement method which is applied at the present time. The applied measurement method data 184b is initially set by the measurement method switching control section 159b and is updated as appropriate.

The irradiation/light reception position list 178b stores an irradiation position and a measurement light reception position selected as a result of the blood vessel type irradiation/light reception position selection process for use in the blood vessel type 179b, and stores an irradiation position and a measurement light reception position selected as a result of the non-blood vessel type irradiation/light reception position selection process for use in the non-blood vessel type 180b. The list for use in the blood vessel type 179b is a data table in which an irradiation position (the measurement light emitting element 52-1) and a measurement light reception position (the measurement light receiving element 54-1) are set in correlation with a blood vessel measurement point number in the same manner as in the irradiation/light reception position list 178 illustrated in FIG. 10. On the other hand, the list for use in the non-blood vessel type 180b is a data table in which an irradiation position (the measurement light emitting element 52-2) and a measurement light reception position (the measurement light receiving element 54-2) are set in correlation with a non-blood vessel part measurement point number.

The measured value data 182b stores a blood glucose level calculated by the component value calculation section 156b in the same manner as in the first embodiment, but sets a blood glucose level calculated at each blood vessel measurement point during a "blood vessel type" measurement, and sets a blood glucose level calculated at each non-blood vessel part measurement point in correlation with a corresponding non-blood vessel part measurement point number after switching to the "non-blood vessel type".

Flow of Process

Figure 18:
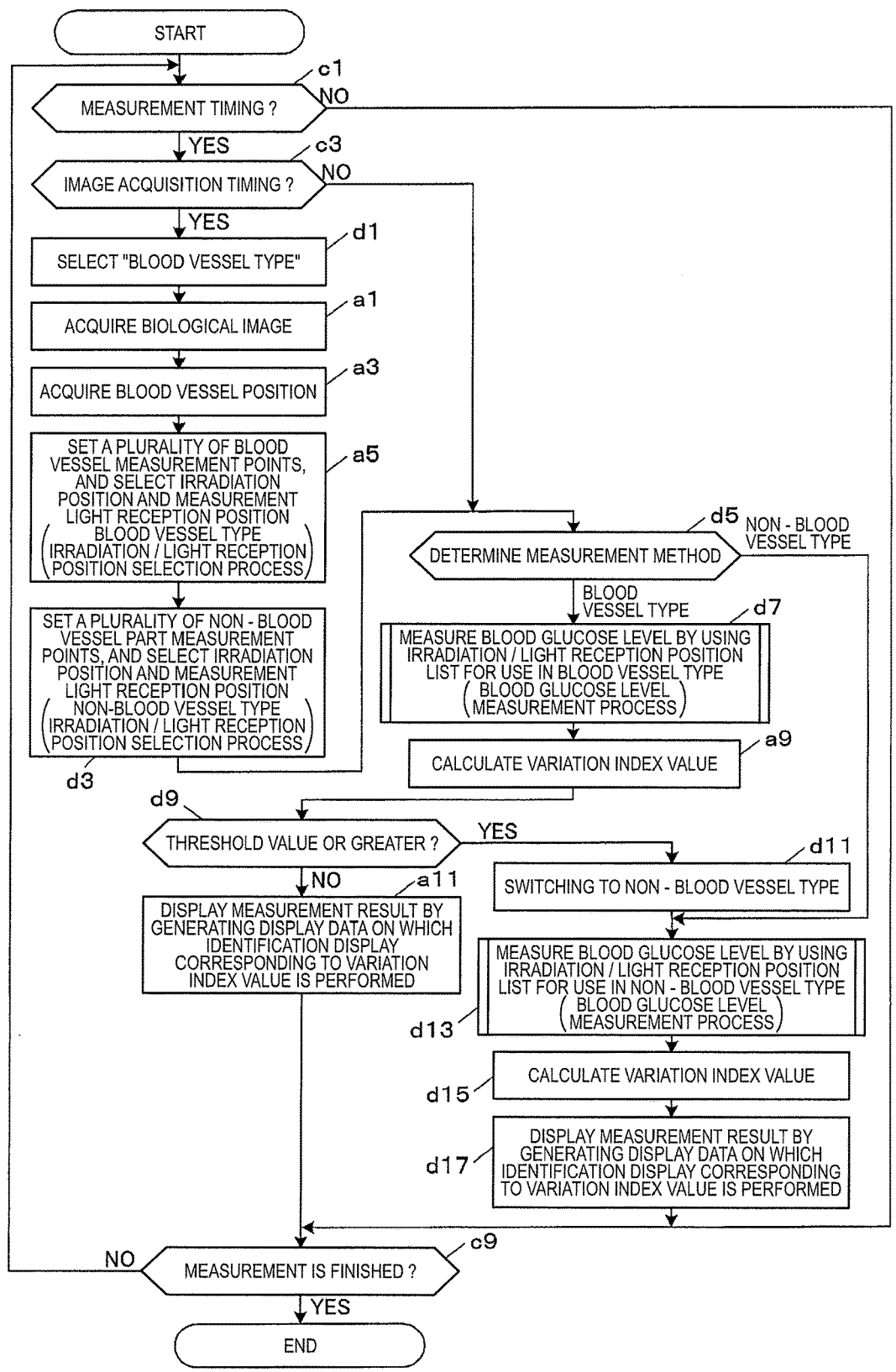
FIG. 18 is a flowchart illustrating process procedures of a third measurement process.

FIG. 18 is a flowchart illustrating process procedures of the third measurement process. The process described here may be performed by the processing unit 150b reading and executing the third measurement process program 171b from the storage unit 170b.

As illustrated in FIG. 18, in the third measurement process, the "blood vessel type" is selected as an applied measurement method at the image acquisition timing (step c3: YES), and the applied measurement method data 184b is initially set (step d1). After a biological image and a blood vessel position are acquired through this process, the "blood vessel type" having the higher priority is first applied. In step a5, the irradiation/light reception position selection section 154b performs a blood vessel type irradiation/light reception position selection process so as to generate the irradiation/light reception position list as a list for use in the blood vessel type 179b, and then performs a non-blood vessel type irradiation/light reception position selection process so as to select irradiation positions and measurement light reception positions for each of a plurality of non-blood vessel part measurement points (step d3). At this time, the irradiation/light reception position selection section 154b assigns a non-blood vessel part measurement point number to each non-blood vessel part measurement point, and generates the irradiation/light reception position list for use in the non-blood vessel type 180b by correlating a light emitting element number of the measurement light emitting element 52-2 and a light receiving element number of the measurement light receiving element 54-2.

Next, the measurement method switching control section 159b refers to the applied measurement method data 184b and determines a measurement method which is being applied (step d5). If a measurement method is the "blood vessel type", the flow proceeds to step a7, and if a measurement method is "non-blood vessel type", the flow proceeds to step d13.

In step d7, a blood glucose level measurement process is performed by using the irradiation/light reception position list for use in the blood vessel type 179b. The blood glucose level measurement process here may be performed in the same procedures as those of the blood glucose level measurement process (refer to FIG. 12) described in the first embodiment. Then, the variation index value calculation section 157b calculates a variation index value on the basis of blood glucose levels at each blood vessel measurement point by using the measured value data 182b (step a9).

Next, the measurement method switching control section 159b performs a threshold value process on the variation index value calculated in step a9, and performs control for switching an applied measurement method depending on whether or not the variation index value is equal to or greater than a predetermined threshold value. In other words, if the variation index value is smaller than the threshold value (step d9: NO), a measurement method is not switched, and the flow proceeds to step a11 where the display data generation section 158 performs control so that display data 183 on which identification display corresponding to the variation index value calculated in step a9 is performed is generated and a measurement result is displayed on the display unit 130.

On the other hand, if the variation index value is equal to or greater than the threshold value (step d9: YES), the measurement method switching control section 159b switches a measurement method to the "non-blood vessel type", and updates the applied measurement method data 184b (step do11), and the flow proceeds to step d13. Through the process in step d11, an applied measurement method is switched to the "non-blood vessel type". In addition, in step d13, a blood glucose level measurement process is performed. The blood glucose level measurement process here may be performed in the same procedures as those of the blood glucose level measurement process (refer to FIG. 12) described in the first embodiment, and, in this case, the irradiation/light reception position list for use in the non-blood vessel type 180b is used. In addition, the processes of the loop A are performed at each non-blood vessel part measurement point.

Then, the variation index value calculation section 157b calculates a variation index value on the basis of blood glucose levels at each non-blood vessel part measurement point by using the measured value data 182b (step d15), and the display data generation section 158 performs control so that display data 183 on which identification display corresponding to the variation index value calculated in step a15 is performed is generated and a measurement result is displayed on the display unit 130 (step d17).

As described above, according to the third embodiment, right after a biological image is captured and a blood vessel position is acquired, the "blood vessel type" having high accuracy can be preferentially applied so that a measurement is performed, and an applied measurement method can be switched to the "non-blood vessel type" according to a variation index value.

In addition, as described above, in a case of the "non-blood vessel type", measurement accuracy is stable and thus does not vary much, and therefore the process in step d15 may be omitted. In this case, measurement accuracy in the "non-blood vessel type" may be defined in advance, and the process in step d17 may be performed by using this in a fixed manner so that the display data 183 is generated and displayed.

In addition, in the third embodiment, a "blood vessel type" measurement and a "non-blood vessel type" measurement are performed in a switching manner. In contrast, there may be a configuration in which both of the "blood vessel type" measurement and the "non-blood vessel type" measurement are performed at all times, and display data is generated and displayed by using a measurement result having a smaller variation index value. In addition, a switching operation of a measurement method may be received, and either the "blood vessel type" or the "non-blood vessel type" may be selected and applied.

In the third embodiment, a description has been made of a case where two measurement methods are switched, but three or more measurement methods may be switched. In this case, priority may be set to each measurement method, and the measurement methods may be switched in an order of the priority if a variation index value is great.

In the first to third embodiments, a description has been made of a case of calculating a variation index value of blood glucose levels which are simultaneously obtained at a plurality of positions (blood vessel measurement points/non-blood vessel part measurement points). In contrast, a plurality of measurements are performed for a predetermined unit time, and a variation index value of a plurality of obtained blood glucose levels may be calculated. The unit time is set to a short period of time to an extent of the blood glucose levels being regarded to be the same as each other.

As a measurement method of a blood glucose level, measurement methods other than the exemplified "blood vessel type" and "non-blood vessel type" may be employed as appropriate. Such measurement methods may be selectively applied, and a measurement may be performed. A variation index value in this case may be calculated on the basis of blood glucose levels which are simultaneously obtained at a plurality of positions, and may be calculated on the basis of a plurality of blood glucose levels which are obtained for a unit time.

As other measurement methods, for example, there may be a measurement method using characteristics in which, if a blood glucose level increases, a refractive index of a living body increases, and thus a scattering coefficient decreases. In this measurement method, measurement light is incident to the skin surface, and light is received at a plurality of light reception positions having different distances from a light source. Since light reaches farther as the scattering coefficient is smaller, a blood glucose level can be measured by comparing light reception results (intensities of received light) at the respective light reception positions. In addition, if a blood glucose level changes, the fact is known that conductivity, thermal conductivity, or the like of a living body varies. A measurement method may be employed in which such a change is measured, and thus a blood glucose level is measured.

In the first to third embodiments, a case has been described in which a blood glucose level is mainly measured, but the invention is also applicable to a case where extracellular components such as other blood components are measured. For example, the present embodiment is applicable to measurements of levels of enzymes such as glutamic pyruvic transaminase (GPT), levels of proteins in blood plasma such as albumin, cholesterol levels, or lactic acid values.

In addition, the invention is also applicable to a case of measuring a living tissue state as biological information of the subject 2. For example, the invention is also applicable to a case where ultrasonic waves are applied toward a living body of a subject as irradiation waves and a blood vessel diameter is measured as a living tissue state, or a case where blood pressure is measured (estimated) on the basis of blood vessel diameter changes.

Figure 19:
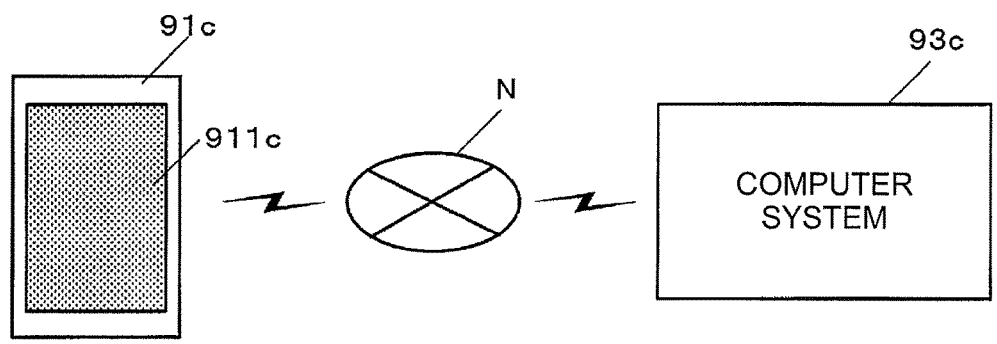
FIG. 19 is a diagram illustrating a system configuration example in a modification example.

A system configuration of the biological information processing apparatus is not limited to the configuration described in the first embodiment. FIG. 19 is a diagram illustrating a system configuration example in a modification example. As illustrated in FIG. 19, there may be a system configuration in which a wearable apparatus 91*c* is constituted by using an electronic apparatus having a touch panel 911*c* which is also used as a display unit, and is connected to a computer system 93*c* so as to perform wired communication or wireless communication therewith.

In this case, the computer system 93*c* includes at least a calculation section (the variation index value calculation section 157 or 157*b*) which calculates a variation index value on the basis of a plurality of measured values obtained by measuring blood glucose levels of a user of the wearable apparatus 91*c*, a generation section (the display data generation section 158) which generates display data on which identification display corresponding to the variation index value is performed, and a transmission control section which controls transmission of the display data to the wearable apparatus 91*c*. The computer system 93*c* calculates a variation index value on the basis of a plurality of values (blood glucose levels) measured by an external apparatus (not illustrated), and generates display data which is then transmitted to the wearable apparatus 91*c*. In a case of the configuration in which a plurality of measured values are acquired from an external apparatus, a mobile phone, a smart phone, a tablet computer, or the like may be used as the wearable apparatus 91*c*.

In addition, a plurality of measured values are not only acquired from an external apparatus but may also be obtained through a measurement performed by the wearable apparatus 91*c*. The wearable apparatus 91*c* in this case, which can be implemented by using, for example, the touch panel 18 and the sensor module 50 in the biological information processing apparatus 10 illustrated in FIG. 1, transmits a light reception result to the computer system 93*c* and displays display data which is received from the computer system 93*c*. In addition, the computer system 93*c* includes functional sections (the absorption spectrum generation section and the component value calculation section) which generates an absorption spectrum on the basis of the light reception result received from the wearable apparatus 91*c*, and calculate a blood glucose level. Alternatively, the process of generating an absorption spectrum and calculating a blood glucose level may be performed by the wearable apparatus 91*c*. Data which is necessary in a process performed by each functional section is stored in the computer system 93*c* or the wearable apparatus 91*c* having a corresponding functional section as appropriate.

What is claimed is:

1. A biological information processing method comprising:
   calculating, by a processor in communication with an image sensor, a variation index value on the basis of a plurality of measured values obtained by measuring biological information of a subject with the image sensor; and
   determining, by the processor, whether the variation index value is at or above a threshold value;
   in response to the variation index value being at or above the threshold value, performing, with the image sensor, measurements conducted at positions on the subject where blood vessel biological measurements cannot be performed due to the lack of a blood vessel detected by the image sensor, and calculating an updated variation index value on the basis of non-blood vessel type biological measurements; and
   generating display data on a display screen, including a measurement result and an identification display corresponding to the variation index value.

2. The biological information processing method according to claim 1, wherein
   the measured value is obtained by applying irradiation waves toward a living body and measuring a predetermined living tissue state or a component in extracellular fluid,
   a plurality of measured values are obtained through a single measurement, and
   the calculating of the variation index value includes calculating the variation index value related to the single measurement.

3. The biological information processing method according to claim 2, further comprising:
   storing a measurement result and the variation index value related to each measurement in correlation with a measurement time,
   wherein the generating of the display data includes generating data for displaying a graph which indicates a time-series change in a range corresponding to the variation index value and the measurement result related to each measurement.

4. The biological information processing method according to claim 2, further comprising:
   acquiring the plurality of measured values by performing a measurement using either one of a first measurement method and a second measurement method in which at least measurement object sites are different from each other.

5. The biological information processing method according to claim 4, wherein the measurement includes:
   performing a measurement using one of the first measurement method and the second measurement method according to a priority which is set in advance, and switching to the other measurement method on the basis of the variation index value.

6. The biological information processing method according to claim 1, further comprising:
acquiring the plurality of measured values by measuring the biological information.

7. A biological information processing apparatus comprising:
an image sensor on a wearable apparatus, the image sensor configured to detect biological measurements of a subject, the biological measurements in the form of blood vessel biological measurements and non-blood vessel biological measurements, the non-blood vessel biological measurements being measurements conducted at positions on the subject where blood vessel biological measurements cannot be performed due to the lack of a blood vessel detected by the image sensor;
a processor that:
calculates a variation index value on the basis of a plurality of measured values obtained by the blood vessel biological measurements; and
calculates an updated variation index value based on the non-blood vessel biological measurements in response to the variation index value being at or above a threshold value; and
a display that displays a measurement result and an identification display corresponding to the variation index value.

8. A computer system which is connected to a wearable apparatus so as to perform communication therewith, the system comprising:
an image sensor, the image sensor configured to detect biological measurements of a user of the wearable apparatus, the biological measurements in the form of blood vessel biological measurements and non-blood vessel biological measurements, the non-blood vessel biological measurements being measurements conducted at positions on the user where blood vessel biological measurements cannot be performed due to the lack of a blood vessel detected by the image sensor;
a processor configured to:
calculate a variation index value on the basis of a plurality of measured values obtained by measuring biological information of the user of the wearable apparatus; and
calculate an updated variation index value based on the non-blood vessel biological measurements in response to the variation index value being at or above a threshold value
a display configured to generate display data which is used to display a measurement result and an identification display corresponding to the variation index value; and
a transmission control section that performs control for transmitting the display data to the wearable apparatus.

9. A wearable apparatus comprising:
an image sensor;
a processor in communication with the image sensor, the processor configured to:
calculate a variation index value on the basis of a plurality of measured values obtained by measuring biological information of a user; and
determine whether the variation index value is at or above a threshold value,
wherein in response to the variation index value being at or above the threshold value:
the image sensor performs measurements conducted at positions on the user where blood vessel biological measurements cannot be performed due to the lack of a blood vessel detected by the image sensor, and
the processor calculates an updated variation index value on the basis of non-blood vessel type biological measurements; and
a display configured to display an identification display corresponding to the variation index value on a measurement result and the measurement result.

10. The wearable apparatus according to claim 9, further comprising:
the image sensor being configured to obtain the measured value by applying irradiation waves toward a living body of a user and measuring a predetermined living tissue state or a component in extracellular fluid.

11. A biological information processing method comprising:
performing, with an image sensor on a wearable apparatus, blood vessel biological measurements of a subject;
calculating, by a processor in communication with the image sensor, a variation index value on the basis of the blood vessel biological measurements;
determining, by the processor, whether the variation index value is at or above a threshold value;
in response to the variation index value being at or above the threshold value, performing, with the image sensor, non-blood vessel type biological measurements of the subject, the non-blood vessel type biological measurements being measurements conducted at positions on the subject where blood vessel biological measurements cannot be performed due to the lack of a blood vessel detected by the image sensor, and calculating an updated variation index value on the basis of non-blood vessel type biological measurements; and
generating display data on a display screen, including a measurement result and an identification display corresponding to the variation index value or the updated variation index value.

* * * * *